US007781183B2

(12) United States Patent
Bavari et al.

(10) Patent No.: US 7,781,183 B2
(45) Date of Patent: Aug. 24, 2010

(54) INHIBITION OF ANTHRAX LETHAL FACTOR PROTEASE

(75) Inventors: Sina Bavari, Frederick, MD (US); Rekha G. Panchal, Frederick, MD (US); Ann Hermone, Frederick, MD (US); Tam Nguyen, Gaithersburg, MD (US); Rick Gussio, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1434 days.

(21) Appl. No.: 11/017,771

(22) Filed: Dec. 22, 2004

(65) Prior Publication Data

US 2005/0251345 A1 Nov. 10, 2005

Related U.S. Application Data

(60) Provisional application No. 60/533,375, filed on Dec. 24, 2003, provisional application No. 60/535,180, filed on Jan. 6, 2004.

(51) Int. Cl.

| | |
|---|---|
| ***C12Q 1/37*** | (2006.01) |
| ***C12N 9/50*** | (2006.01) |
| ***C07D 233/00*** | (2006.01) |
| ***G01N 33/53*** | (2006.01) |

(52) U.S. Cl. .......................... 435/23; 435/7.1; 435/219; 548/335.1

(58) Field of Classification Search ....................... None
See application file for complete search history.

(56) References Cited

U.S. PATENT DOCUMENTS 5,725,878 A * 3/1998 Al-Razzak et al. .......... 424/456

OTHER PUBLICATIONS

Horvath, Dragos. A virtual screening approach applied to the search fro trypanothione reductase inhibitors. Journal of Medicinal Chemistry, 1997, vol. 40, pp. 2412-2423.*

Soelaiman et al. Structure-based inhibitor discovery against adenylyl cyclase toxins from pathogenic bacteria that cause anthrax and whooping cough. The Journal of Biological Chemistry, vol. 278, Apr. 3, 2003, pp. 25990-25997.*

Montecucco et al. Stop the killer: how to inhibit the anthrax lethal factor metalloprotease. Trends in Biochemical Science, vol. 29, Jun. 6, 2004, pp. 292-295.*

DTP Diversity Set Information for NSC 12155, Mar. 28, 2006.

DTP Diversity Set Information for NSC 317881, Mar. 28, 2006.

DTP Diversity Set Information for NSC 317884, Mar. 28, 2006.

DTP Diversity Set Information for NSC 341909, Mar. 28, 2006.

DTP Diversity Set Information for NSC 357756, Mar. 28, 2006.

Panchal et al. (2004) "Identification of small molecule inhibitors of anthrax lethal factor" Nature Structural and Molecular Biology 11(1):67-72.

Montecucco et al. (2004) "Stop the killer: how to inhibit the anthrax lethal factor metalloprotease" Trends in Biochemical Sciences 29(6):282-285.

International Search Report and Written Opinion for PCT/US2004/043273, Dec. 29, 2005.

* cited by examiner

*Primary Examiner*—Marjorie Moran
*Assistant Examiner*—Russell S Negin
(74) *Attorney, Agent, or Firm*—Elizabeth Arwine

(57) ABSTRACT

Disclosed herein is a pharmacophore model for inhibiting anthrax lethal factor protease activity which comprises a first aromatic center A, a second aromatic center B, a first polar center C, a second polar center D, a third polar center E, and a neutral linker F. Also disclosed are small molecules fitting the pharmacophore model and compositions and methods of using thereof.

6 Claims, 7 Drawing Sheets

INHIBITION OF ANTHRAX LETHAL FACTOR PROTEASE

CROSS REFERENCE TO RELATED APPLICATIONS

This application claims the benefit of U.S. Provisional Patent Application Ser. Nos. 60/533,375, filed 24 Dec. 2003, and 60/535,180, filed 6 Jan. 2004, listing Sina Bavari and Rekha G. Panchal, as joint inventors, which are herein incorporated by reference in their entirety.

ACKNOWLEDGMENT OF GOVERNMENT SUPPORT

This invention was made by employees of the United States Army. The government has rights in the invention.

BACKGROUND OF THE INVENTION

1. Field of the Invention

The present invention generally relates to inhibitors of anthrax lethal factor protease activity.

2. Description of the Related Art

Anthrax, a disease caused by *Bacillus anthracis,* has recently been the subject of intense interest because of its use as a biological weapon against human populations.

The inhalation of *B. anthracis* spores is often fatal if the condition is not properly diagnosed and treated with antibiotics during the early stages of infection. In many cases antibiotic regimes may not be effective, especially if there is bacterium overload, which causes large amounts of lethal toxin to be released. Hence, a new level of adjunct treatment is needed to inactivate the toxins released by *B. anthracis.*

Anthrax toxin (AT) consists of three proteins: lethal factor, protective antigen and edema factor, all of which work in concert to kill host cells. Initially, PA binds to an AT receptor on the host cell surface, where it is subsequently cleaved by furin (or furin-like proteases) to produce a 20-kDa N-terminal fragment ($PA_{20}$) and a 63-kDa C-terminal fragment ($PA_{63}$). See Bradley, K. A., et al. (2001) Nature 414:225-229; Scobie, H. M., et al. (2003) PNAS USA 100:5170-5174; Klimpel, K. R., et al. (1992) PNAS USA 89:10277-10281; and Molloy, S. S., et al. (1992) J. Biol. Chem. 267:16396-16402. After cleavage, seven $PA_{63}$ monomers assemble to form a heptameric prepore capable of binding both LF and EF. Upon binding of LF or EF, the entire complex undergoes receptor-mediated endocytosis. It is hypothesized that the acidic endosomal environment causes a conformational change in the $PA_{63}$ heptamer to produce a functional pore that traverses the membrane and translocates the two enzymatic moieties LF and EF into the cell cytosol. EF is a calmodulin-dependent adenylate cyclase; LF is a Zn-dependent metalloprotease that cleaves several members of the MAPKK family near the N terminus. See Leppla, S. H. PNAS USA (1982) 79:3162-3166; Vitale, G. et al. (1998) Biochem. Biophys. Res. Commun. 248:706-711; and Duesbery, N. S. et al. (1998) Science 280:734-737. This cleavage prevents interaction with, and phosphorylation of, downstream MAPK, thereby inhibiting one or more signaling pathways. See Duesbery, N. S. et al. (2001) PNAS USA 98:4089-4094. Through a mechanism that is not yet well understood, this results in the death of the host. Recent studies suggest that the inactivation of p38 MAPK induces apoptosis in LF-exposed macrophages, thereby preventing the release of chemokines and cytokines, and preventing the immune system from responding to the pathogen. See Park, J. M., et al. (2002) Science 297:2048-2051. Based on the current understanding of the mechanism of anthrax toxin, methods may be developed to inhibit various steps in toxin assembly and/or function. In one antitoxin therapy approach, dominant-negative PA mutants have been generated that coassemble with the wild-type PA protein, blocking the translocation of LF and EF across the cell membrane. Such PA mutants are potent inhibitors of anthrax toxin in both cell-based assays and in vivo animal models. See Sellman, B. R., et al. (2001) Science 292:695-697; and Singh, Y., et al. (2001) J. Biol. Chem. 276:22090-22094. In a second approach, a peptide inhibitor that binds to the heptameric PA and prevents the interaction of PA with LF and EF has shown efficacy in animals. See Mourez, M. et al. (2001) Nat. Biotechnol. 19:958-961.

The lethal action of anthrax toxin may also be inactivated by molecules that inhibit the protease activity of LF. So far, the only known small molecule inhibitors of LF are nonspecific hydroxymates that are effective at greater than about 100 μM concentration and more recently reported hydroxymate derivatives of peptide substrate that inhibit LF at nanomolar concentrations. See Hammond, S. E. & Hanna, P. C. (1998) Infect. Immun. 66:2374-2378; and Tonello, F., et al. (2002) Nature 418:386; Turk, B. E. et al. (2004) Nat. Struct. Mol. Biol. 11(1):60-66. Unfortunately, no small molecule (non-peptidic) inhibitors of anthrax lethal factor, which are effective in the low μM range, have been reported.

Thus, a need exists for more effective compounds and methods for preventing intoxication by anthrax lethal factor.

SUMMARY OF THE INVENTION

The present invention generally relates to a pharmacophore model for inhibiting anthrax lethal factor protease activity.

In some embodiments, the present invention provides a pharmacophore model for inhibiting anthrax lethal factor protease activity which comprises a first aromatic center A, a second aromatic center B, a first polar center C, a second polar center D, a third polar center E, and a neutral linker F. In some embodiments, the distance between the first aromatic center A and the neutral linker F is about 4.7 to about 6.7 Å, preferably about 5.7 Å. In some embodiments, the distance between the neutral linker F and the second aromatic center B is about 3.4 to about 4.4 Å, preferably about 3.9 Å. In some embodiments, the distance between first aromatic center A and the first polar center C is about 5.5 to about 7.5 Å, preferably about 6.5 Å. In some embodiments, the distance between the first aromatic center A and the second polar center D is about 4.6 to about 6.6 Å, preferably about 5.6 Å. In some embodiments, the distance between the second aromatic center B and the second polar center D is about 3.6 to about 4.6 Å, preferably about 4.1 Å. In some embodiments, the distance between the second aromatic center B and the third polar center E is about 2.6 to about 3.6 Å, preferably about 3.1 Å. In some embodiments, the distance between the first polar center C and the third polar center E is about 15.6 to about 19.6 Å, preferably about 17.6 Å.

In some embodiments, the present invention provides a pharmacophore model for inhibiting anthrax lethal factor protease activity which comprises a first aromatic center A, a second aromatic center B, a first polar center C, a second polar center D, a third polar center E, and a neutral linker F, wherein the distance between the first aromatic center A and the neutral linker F is about 5.7 Å, the distance between the neutral linker F and the second aromatic center B is about 3.9 Å, the distance between first aromatic center A and the first polar center C is about 6.5 Å, the distance between the first aromatic center A and the second polar center D is about 5.6 Å, the distance between the second aromatic center B and the second polar center D is about 4.1 Å, the distance between the second aromatic center B and the third polar center E is about 3.1 Å, and the distance between the first polar center C and the third polar center E is about 17.6 Å

In some embodiments, the present invention provides a method of inhibiting anthrax lethal factor protease activity which comprises contacting anthrax lethal factor protease with at least one compound fitting a pharmacophore model for inhibiting anthrax lethal factor protease activity which comprises a first aromatic center A, a second aromatic center B, a first polar center C, a second polar center D, a third polar center E, and a neutral linker F. In some embodiments, the distance between the first aromatic center A and the neutral linker F is about 4.7 to about 6.7 Å, preferably about 5.7 Å. In some embodiments, the distance between the neutral linker F and the second aromatic center B is about 3.4 to about 4.4 Å, preferably about 3.9 Å. In some embodiments, the distance between first aromatic center A and the first polar center C is about 5.5 to about 7.5 Å, preferably about 6.5 Å. In some embodiments, the distance between the first aromatic center A and the second polar center D is about 4.6 to about 6.6 Å, preferably about 5.6 Å. In some embodiments, the distance between the second aromatic center B and the second polar center D is about 3.6 to about 4.6 Å, preferably about 4.1 Å. In some embodiments, the distance between the second aromatic center B and the third polar center E is about 2.6 to about 3.6 Å, preferably about 3.1 Å. In some embodiments, the distance between the first polar center C and the third polar center E is about 15.6 to about 19.6 Å, preferably about 17.6 Å. In some embodiments, the compound is selected from the group consisting of NSC 341911, NSC 294206, NSC 300509, NSC 294494, NSC 359465, NSC 354962, NSC 377362, NSC 317881, NSC 317884, NSC 354961, NSC 12155, NSC 317880, NSC 317886, NSC 294200, NSC 294203, NSC 341909, NSC 357756, NSC 369718, NSC 369721, NSC 294201, NSC 290107, NSC 294204, NSC 240898, and NSC 266474.

In some embodiments, the present invention provides a method of inhibiting anthrax lethal factor protease activity which comprises contacting anthrax lethal factor protease with at least one compound selected from the group consisting of NSC 341911, NSC 294206, NSC 300509, NSC 294494, NSC 359465, NSC 354962, NSC 377362, NSC 317881, NSC 317884, NSC 354961, NSC 12155, NSC 317880, NSC 317886, NSC 294200, NSC 294203, NSC 341909, NSC 357756, NSC 369718, NSC 369721, NSC 294201, NSC 290107, NSC 294204, NSC 240898, and NSC 266474.

In some embodiments, the present invention provides a composition comprising at least one compound fitting a pharmacophore model for inhibiting anthrax lethal factor protease activity which comprises a first aromatic center A, a second aromatic center B, a first polar center C, a second polar center D, a third polar center E, and a neutral linker F. In some embodiments, the distance between the first aromatic center A and the neutral linker F is about 4.7 to about 6.7 Å, preferably about 5.7 Å. In some embodiments, the distance between the neutral linker F and the second aromatic center B is about 3.4 to about 4.4 Å, preferably about 3.9 Å. In some embodiments, the distance between first aromatic center A and the first polar center C is about 5.5 to about 7.5 Å, preferably about 6.5 Å. In some embodiments, the distance between the first aromatic center A and the second polar center D is about 4.6 to about 6.6 Å, preferably about 5.6 Å. In some embodiments, the distance between the second aromatic center B and the second polar center D is about 3.6 to about 4.6 Å, preferably about 4.1 Å. In some embodiments, the distance between the second aromatic center B and the third polar center E is about 2.6 to about 3.6 Å, preferably about 3.1 Å. In some embodiments, the distance between the first polar center C and the third polar center E is about 15.6 to about 19.6 Å, preferably about 17.6 Å. In some embodiments, the compound is selected from the group consisting of NSC 341911, NSC 294206, NSC 300509, NSC 294494, NSC 359465, NSC 354962, NSC 377362, NSC 317881, NSC 317884, NSC 354961, NSC 12155, NSC 317880, NSC 317886, NSC 294200, NSC 294203, NSC 341909, NSC 357756, NSC 369718, NSC 369721, NSC 294201, NSC 290107, NSC 294204, NSC 240898, and NSC 266474. In some embodiments, the composition further comprises a pharmaceutically acceptable carrier. In some embodiments, the composition further comprises a supplementary active compound.

In some embodiments, the present invention provides a method of screening a database of compounds for candidate compounds that inhibit anthrax lethal factor protease activity which comprises mapping the compounds to a pharmacophore model for inhibiting anthrax lethal factor protease activity which comprises a first aromatic center A, a second aromatic center B, a first polar center C, a second polar center D, a third polar center E, and a neutral linker F. In some embodiments, the distance between the first aromatic center A and the neutral linker F is about 4.7 to about 6.7 Å, preferably about 5.7 Å. In some embodiments, the distance between the neutral linker F and the second aromatic center B is about 3.4 to about 4.4 Å, preferably about 3.9 Å. In some embodiments, the distance between first aromatic center A and the first polar center C is about 5.5 to about 7.5 Å, preferably about 6.5 Å. In some embodiments, the distance between the first aromatic center A and the second polar center D is about 4.6 to about 6.6 Å, preferably about 5.6 Å. In some embodiments, the distance between the second aromatic center B and the second polar center D is about 3.6 to about 4.6 Å, preferably about 4.1 Å. In some embodiments, the distance between the second aromatic center B and the third polar center E is about 2.6 to about 3.6 Å, preferably about 3.1 Å. In some embodiments, the distance between the first polar center C and the third polar center E is about 15.6 to about 19.6 Å, preferably about 17.6 Å.

In some embodiments, the present invention provides a kit comprising at least one compound fitting a pharmacophore model for inhibiting anthrax lethal factor protease activity which comprises a first aromatic center A, a second aromatic center B, a first polar center C, a second polar center D, a third polar center E, and a neutral linker F. In some embodiments, the distance between the first aromatic center A and the neutral linker F is about 4.7 to about 6.7 Å, preferably about 5.7 Å. In some embodiments, the distance between the neutral linker F and the second aromatic center B is about 3.4 to about 4.4 Å, preferably about 3.9 Å. In some embodiments, the distance between first aromatic center A and the first polar center C is about 5.5 to about 7.5 Å, preferably about 6.5 Å. In some embodiments, the distance between the first aromatic center A and the second polar center D is about 4.6 to about 6.6 Å, preferably about 5.6 Å. In some embodiments, the distance between the second aromatic center B and the second polar center D is about 3.6 to about 4.6 Å, preferably about 4.1 Å. In some embodiments, the distance between the second aromatic center B and the third polar center E is about 2.6 to about 3.6 Å, preferably about 3.1 Å. In some embodiments, the distance between the first polar center C and the third polar center E is about 15.6 to about 19.6 Å, preferably about 17.6 Å. The kit may further include instructions for use, a device for delivering the compound to a subject, a supplementary active compound, reagents for assaying the activity of anthrax lethal factor protease, or a combination thereof.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein:

FIG. 3 shows the pharmacophore model of the LF inhibitors of the present invention. These data were combined with molecular docking studies of structurally related analogs from 3D database mining studies.

The electron density surrounding NSC 12155 shown in these figures are $2F_0$-$F_c$ difference maps calculated at 2.9 Å resolution.

Figure 5A:
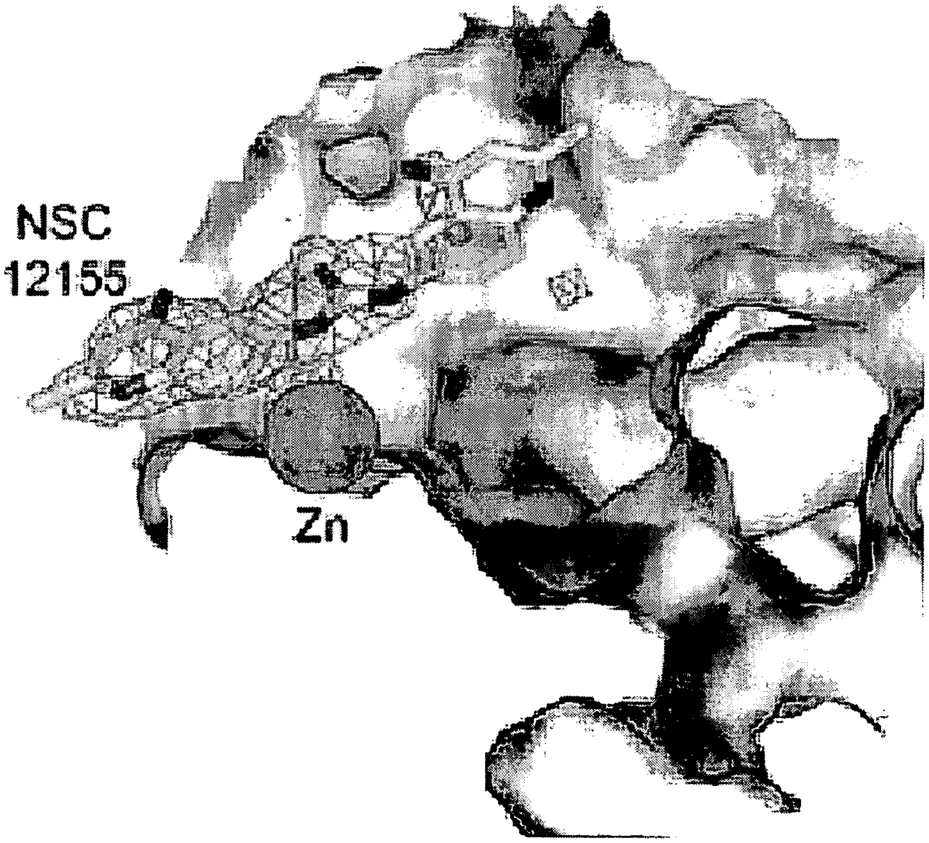
FIG. 5 shows the X-ray crystal structure of the LF-NSC 12155-Zn complex.

FIG. 5A shows a detailed view of the electron density trace and overall model fit of NSC 12155. The color version of this figure may be found in Panchal, et al. (2004) Nature Struct. & Molec. Biol. 11:67-72, which is herein incorporated by reference, wherein the molecular surface of LF is colored by charge (red=negative; blue=positive), with $Zn^{2+}$ (cyan), and the model of the inhibitor molecule NSC 12155 (yellow) is in stick representation. The difference map, $2F_0-F_c$, is contoured at 1.1σ level.

Figure 5B:
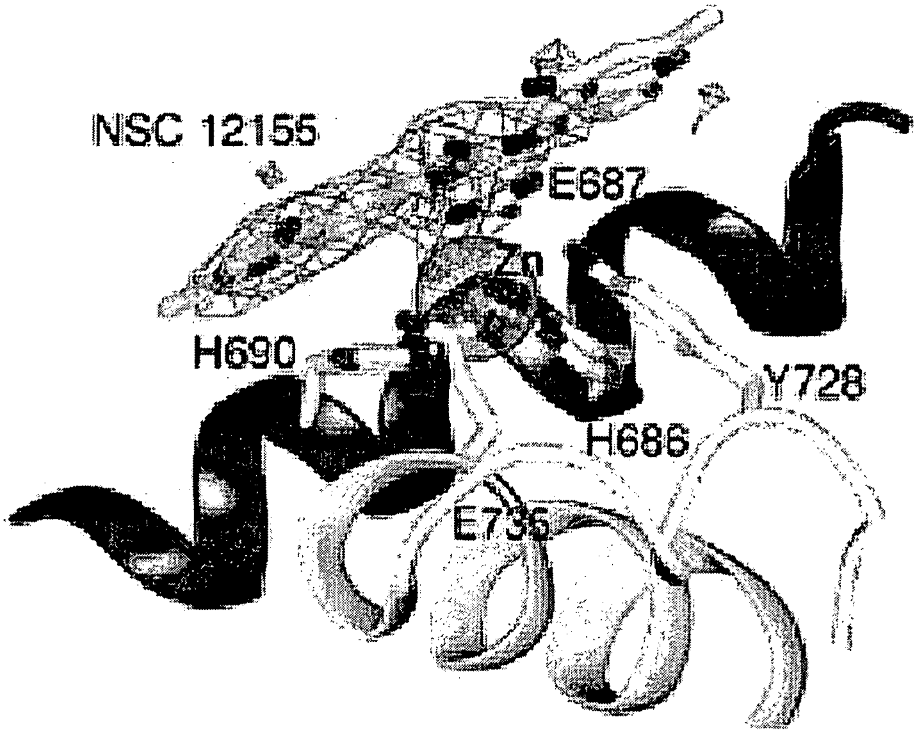

FIG. 5B shows the inhibitor NSC 12155 bound in the active site of LF. The difference map, $2F_0-F_c$ is contoured at 1.0σ. A portion of NSC 12155appears nonrigid owing to a rotatable bond, and almost full electron density coverage is seen for this portion at a contour level of 0.6σ. The color version of this figure may be found in Panchal, et al. (2004) Nature Struct. & Molec. Biol. 11:67-72, which is herein incorporated by reference, wherein inhibitor molecule (yellow), zinc-coordinating residues (H686, H690, E735) and catalytic residues (E687, Y728) are in stick representation; the Cα, atoms of residues 680-694 (green, background) and 726-742 (beige, foreground) are in ribbon representation and the $Zn^{2+}$ ion (cyan) is a lined sphere, and its hydrogen bonds with His 686, His 690 and Glu 735 are represented as aligned small white spheres. These figures were prepared using SPOCK. See the World Wide Web at mackerel.tamu.edu/spock/.

Figure 6:
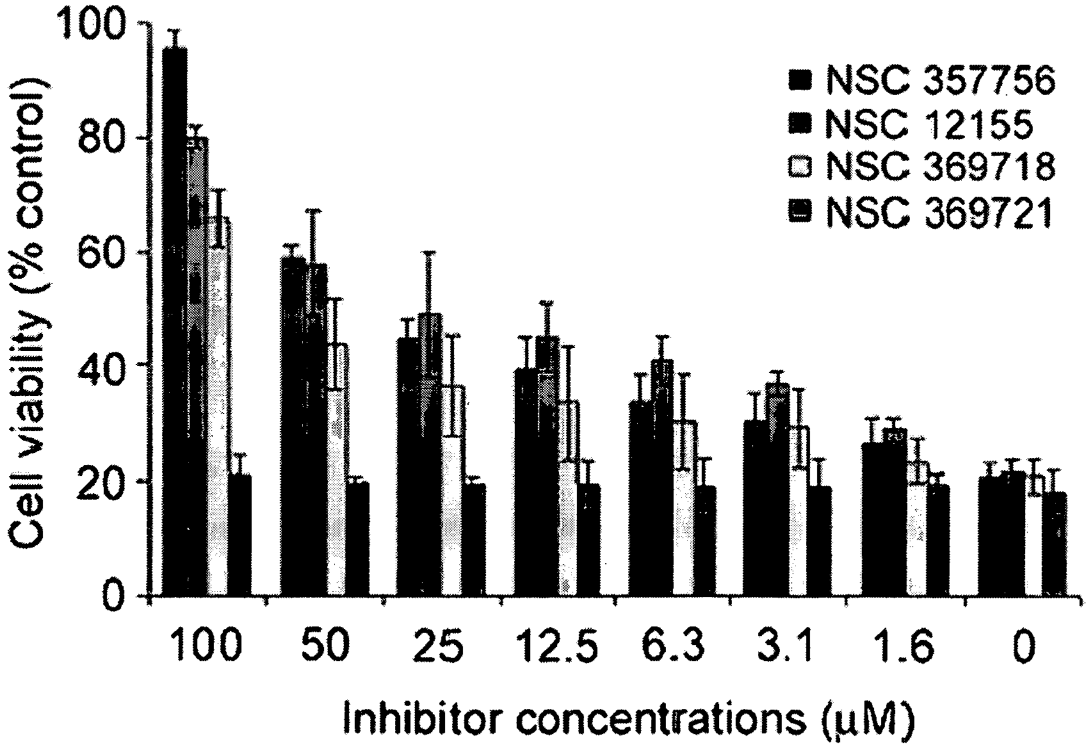

FIG. 6 shows the efficacy of the LF inhibitors in a cell-based toxicity assay.

J774A.1 cells were pretreated with either DMSO control or various concentrations of inhibitors, and then incubated with anthrax lethal toxin. After 4 hours, cell viability was determined with MTT dye. The color version of this figure may be found in Panchal, et al. (2004) Nature Struct. & Molec. Biol. 11:67-72, which is herein incorporated by reference.

DETAILED DESCRIPTION OF THE INVENTION

The present invention provides several small molecule (nonpeptidic) compounds that inhibit anthrax LF protease activity with $K_i$ values in the range of about 0.5 to about 5 μM. As provided herein, a structure-based approach for anthrax therapeutic development was used in parallel with the peptidomimetic approach used by Turk et al. to identify small organic molecules as lead candidates. See Turk, B. E. et al. (2004) Nat. Struct. Mol. Biol. 11(1):60-66, which is herein incorporated by reference. Specifically, molecular diversity screening combined with 3D database searching and molecular modeling was used. The LF X-ray crystal structure reported by Pannifer et al. was useful during the structure-based drug discovery portion of these studies. See Pannifer, A. D. et al. (2001) Nature 414:229-233, which is herein incorporated by reference.

As provided herein high-throughput screening (HTS) of small molecules from the NCI Diversity Set was conducted to identify LF inhibitors. Hits identified from the HTS were verified with an HPLC-based assay known in the art. Afterwards, X-ray crystallography and molecular modeling (conformational sampling, database mining and molecular docking) were used to identify additional lead therapeutics. Based on an iterative process of compound selection and biological testing, a pharmacophore for LF inhibitors as described herein was developed.

Figure 1A:
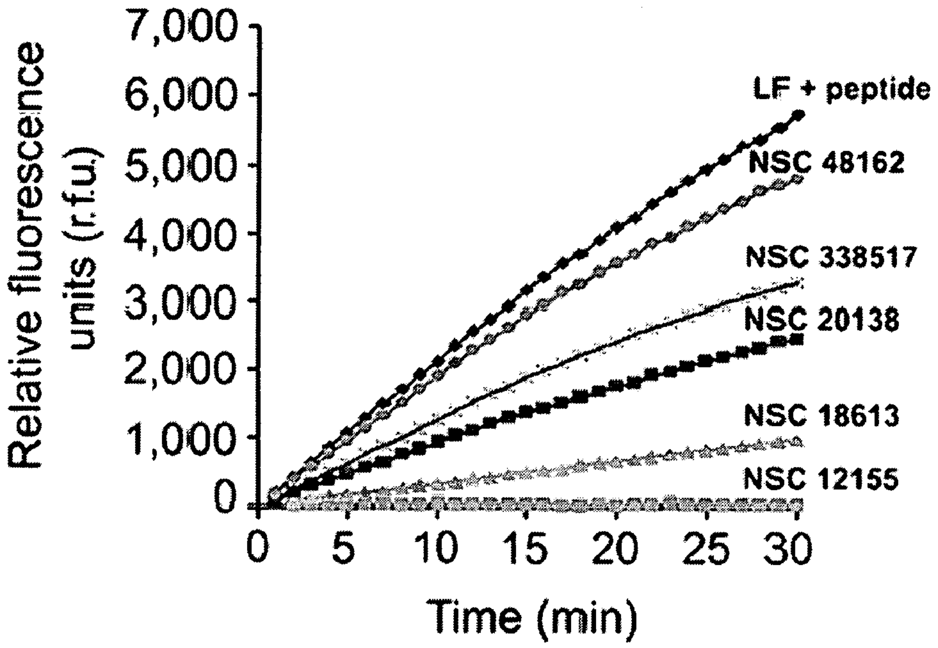
FIG. 1A shows representative data from a fluorescent plate reader assay showing different degrees of inhibition by compounds from the NCI Diversity Set.
Figure 1B:
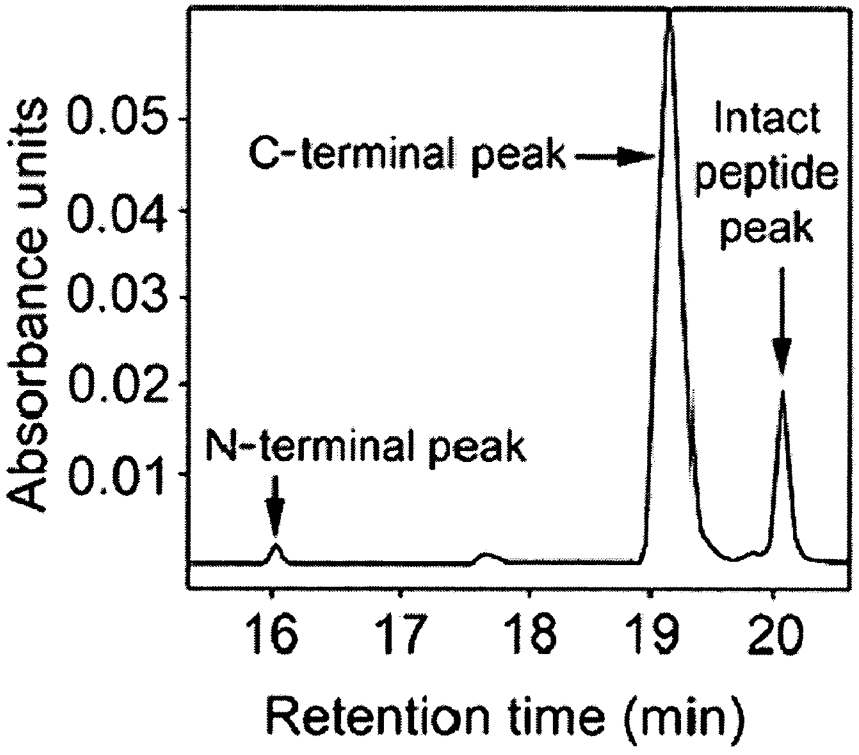
FIG. 1B shows an HPLC-based assay without inhibitor, showing the N- and C-terminal cleavage products after incubation of the substrate with LF for 30 minutes.
Figure 1C:
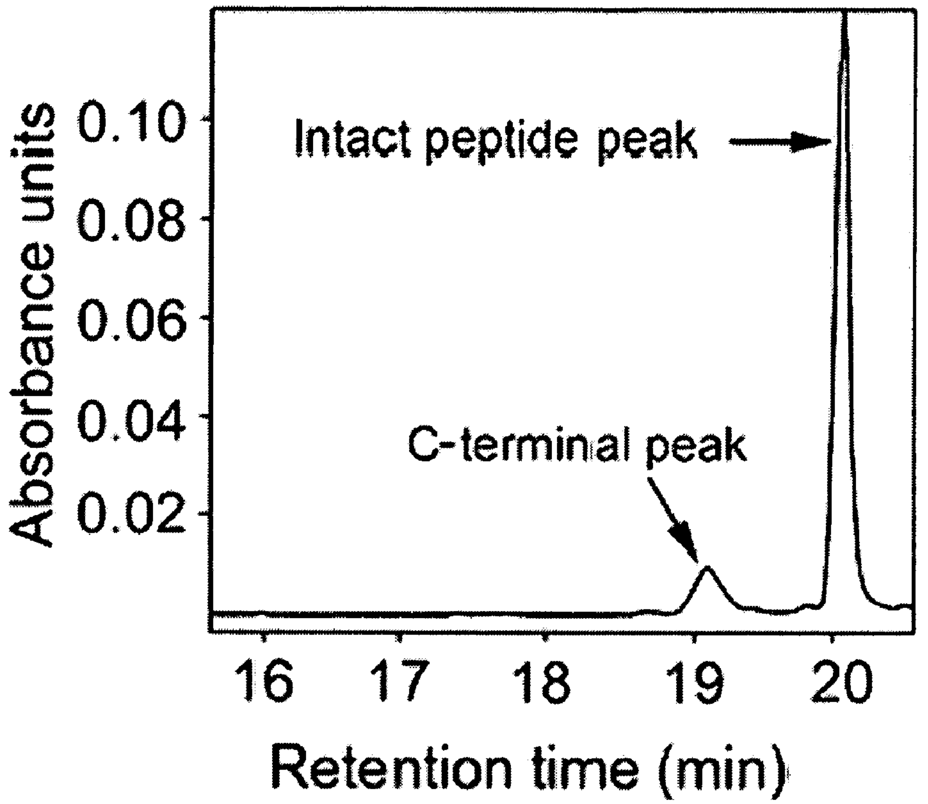
FIG. 1C shows an HPLC-based assay with inhibitor NSC 12155 showing a reduced C-terminal peak area at 365 nm, indicating strong inhibition of LF activity.
Figure 2A:
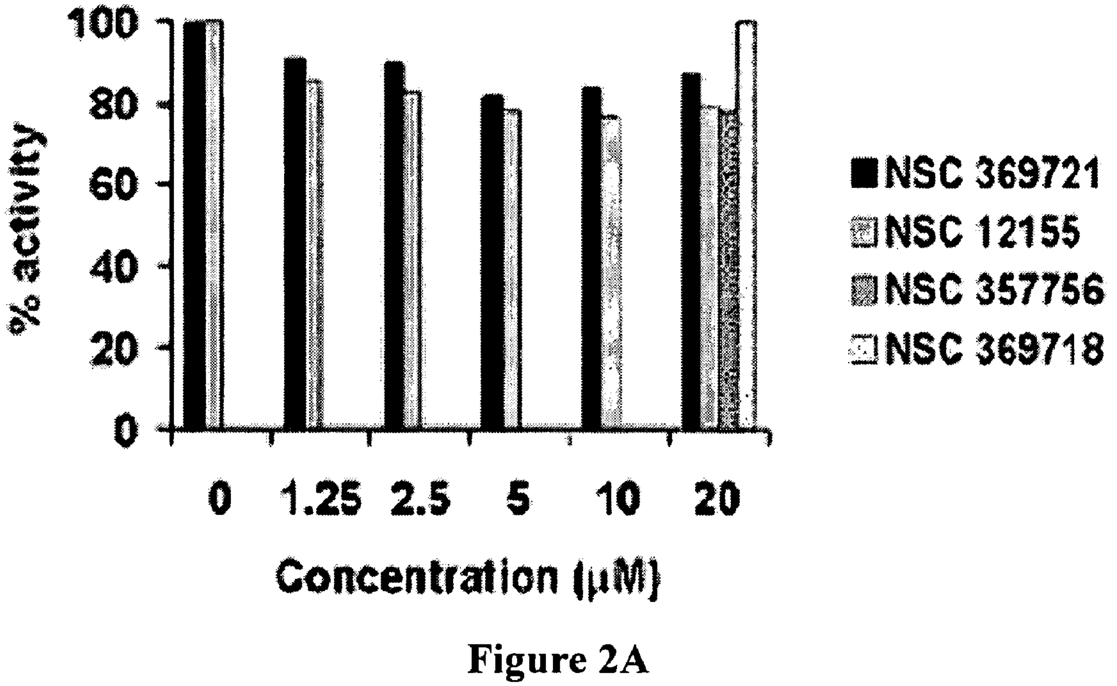
FIG. 2A shows the effect of LF inhibitors on elastase.
Figure 2B:
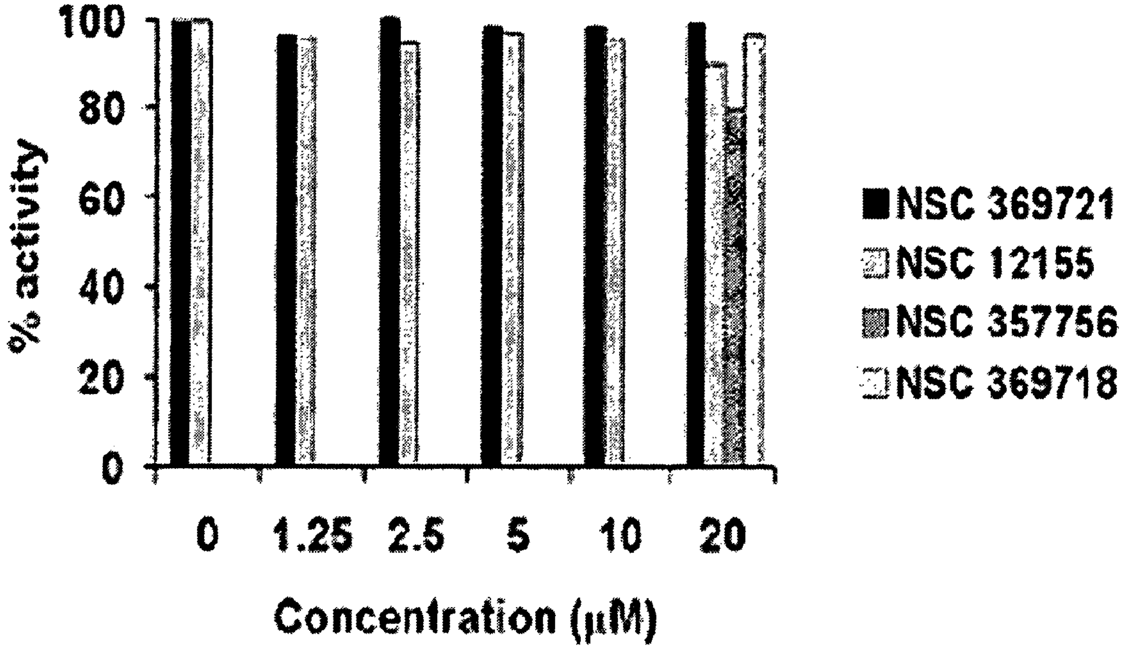
FIG. 2B shows the effect of LF inhibitors on thermolysin.
Figure 2C:
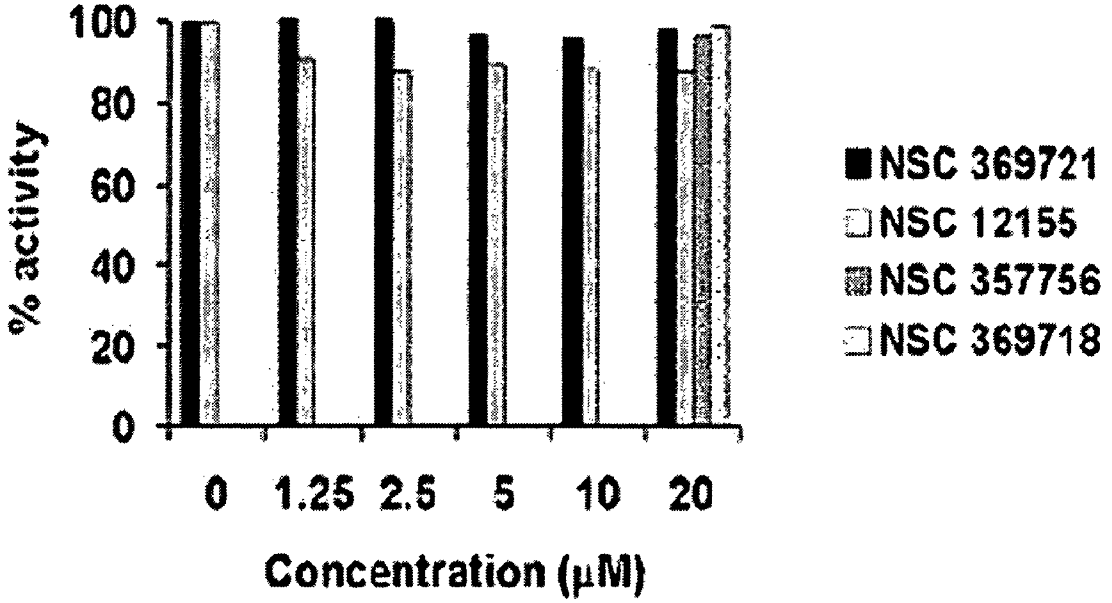
FIG. 2C shows the effect of LF inhibitors on papain.

To screen and identify compounds that inhibit LF activity, a high-throughput fluorescence-based assay was developed. An optimized peptide with a fluorogenic coumarin group at the N terminus and a 2,4-dinitrophenyl (dnp) quenching group at the C terminus was used as LF substrate for in vitro assays as provided in The color version of this figure may be found in Panchal, et al. (2004) Nature Struct. & Molec. Biol. 11:67-72, which is herein incorporated by reference. After cleavage by LF, fluorescence increased (excitation and emission wavelengths, 325 and 394 nm, respectively). After standardization of the high-throughput assay, the 1,990 compounds in the NCI Diversity Set were tested. See FIG. 1A. Compounds that showed greater than about 75% inhibition were selected for validation using an HPLC-based assay. This eliminated false positives due to fluorescence quenching by some of the test compounds. Using the HPLC-based assay, compounds that showed greater than about 50% inhibition were selected for further study. See FIG. 1B and FIG. 1C. The HPLC assay, in addition to eliminating false positives, was a more rigorous test of LF inhibition, as a lower inhibitor concentration (about 20 μM) was used (compared with 100-μM concentration used in the fluorescence-based assays). Furthermore, the identified LF inhibitors did not inhibit a range of different proteases, thus confirming that these compounds did not inhibit LF promiscuously. FIG. 2A shows the effect of LF inhibitors on elastase. FIG. 2B shows the effect of LF inhibitors on thermolysin. FIG. 2C shows the effect of LF inhibitors on papain.

As provided herein, 19 compounds were identified with greater than about 50% LF inhibition (at about 20 μM inhibitor concentration) from the NCI Diversity Set screen. These included several organometallic and charged molecules. As provided herein, only relatively small organic compounds were chosen for structure-based studies, as these molecules are more likely to show therapeutic potential. However, larger compounds may be applied according to the disclosure herein.

Figure 3A:
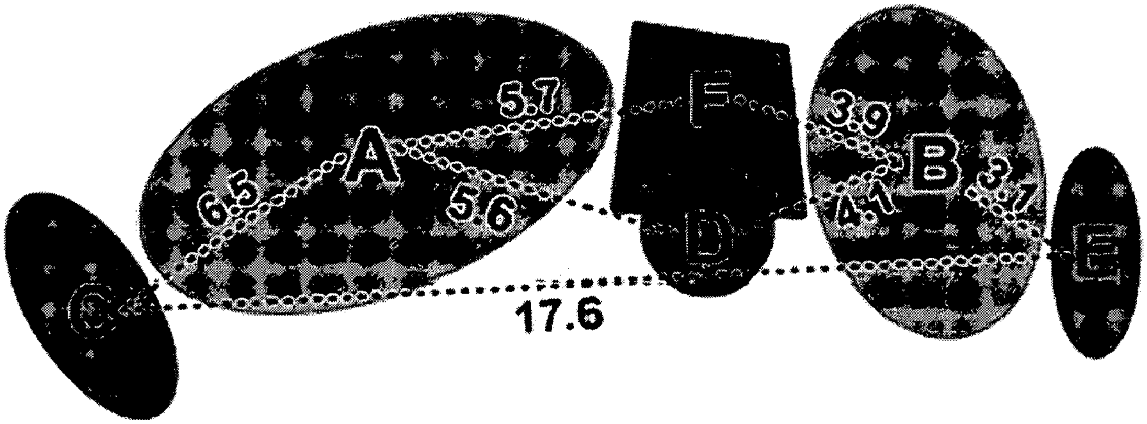
In FIG. 3A, the dashed lines depict the distances between the various centroids of the pharmacophore centers. The color version of this figure may be found in Panchal, et al. (2004) Nature Struct. & Molec. Biol. 11:67-72, which is herein incorporated by reference, wherein green ellipses (A and B) are aromatic centers; red ellipses (C, D and E) are polar centers (hydrogen bond donors or acceptors); blue region (F) is a neutral linker that may include a variety of polar or hydrophobic groups.

The conformational spaces of two leads, NSC 12155 and NSC 357756, were subsequently explored to generate multiple pharmacophoric hypotheses, which were then used in 3D database mining studies to identify additional LF inhibitors. Several iterations of this process were conducted, which comprised 3D database mining of the entire NCI repository (as well as commercially available chemical repositories including the Available Chemicals Directory, MayBridge and BioByte) and subsequent biological testing, to identify new inhibitors. During this process greater than about 60 compounds were tested and most of them were inactive. However, six of the compounds, which showed a range of LF inhibitory potency, were used to develop and refine the pharmacophore model of the present invention as shown in FIG. 3A.

As provided herein, the present invention provides a pharmacophore model for inhibiting anthrax lethal factor protease activity which comprises a first aromatic center A, a second aromatic center B, a first polar center C, a second polar center D, a third polar center E, and a neutral linker F. In some embodiments, the distance between the first aromatic center A and the neutral linker F is about 4.7 to about 6.7 Å, preferably about 5.7 Å. In some embodiments, the distance between the neutral linker F and the second aromatic center B is about 3.4 to about 4.4 Å, preferably about 3.9 Å. In some embodiments, the distance between first aromatic center A and the first polar center C is about 5.5 to about 7.5 Å, preferably about 6.5 Å. In some embodiments, the distance between the first aromatic center A and the second polar center D is about 4.6 to about 6.6 Å, preferably about 5.6 Å. In some embodiments, the distance between the second aromatic center B and the second polar center D is about 3.6 to about 4.6 Å, preferably about 4.1 Å. In some embodiments, the distance between the second aromatic center B and the third polar center E is about 2.6 to about 3.6 Å, preferably about 3.1 Å. In some embodiments, the distance between the first polar center C and the third polar center E is about 15.6 to about 19.6 Å, preferably about 17.6 Å.

Figure 3B:
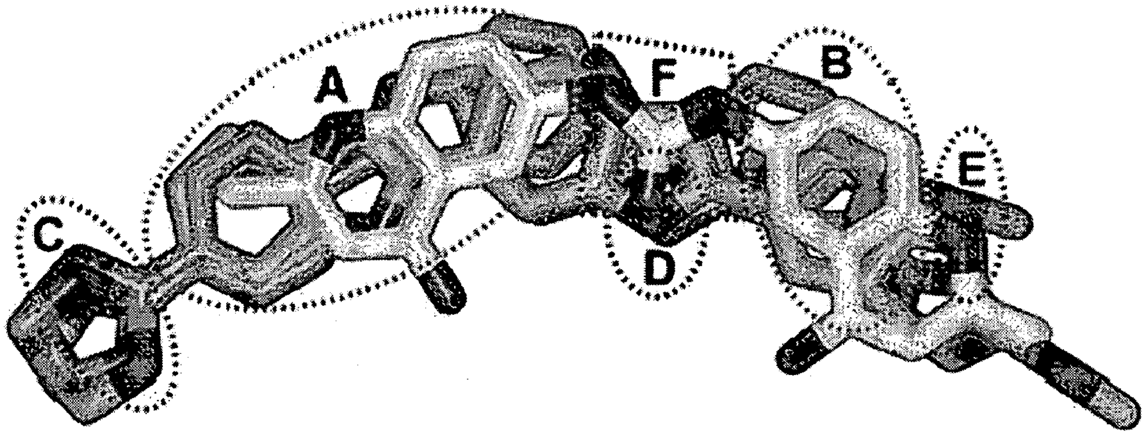
FIG. 3B shows the pharmacophoric overlap of LF inhibitors (stick rendering) and their correspondence to the pharmacophore shown in FIG. 3A. The color version of this figure may be found in Panchal, et al. (2004) Nature Struct. & Molec. Biol. 11:67-72, which is herein incorporated by reference, wherein the pharmacophoric overlap regions of compounds are highlighted in dashed lines (green, aromatic centers; blue, neutral (polar or hydrophobic groups acceptable) linker region; red, polar centers and for all structures: nitrogen, blue; oxygen, red. Carbon atoms for NSC 12155, yellow; for NSC 357756, magenta; for NSC 369721, green; for NSC 369728, light blue. The pharmacophore is based on the energy-refined X-ray conformation of NSC 12155 bound to LF.

A 3D superimposition of four of the most potent LF inhibitors (NSC 12155, NSC 357756, NSC 369718 and NSC 369721), as shown in FIG. 3B, exhibits an excellent overlay of the polar heteroatoms and hydrophobic substituents of these molecules. The chemical structures of a range of identified LF inhibitors and their percent inhibition at about 20 μM concentration are shown in Table 1 as follows:

TABLE 1

| Structure | NSC number | % inhibition | $K_i$ (μM) | Inhibition type |
|---|---|---|---|---|
| 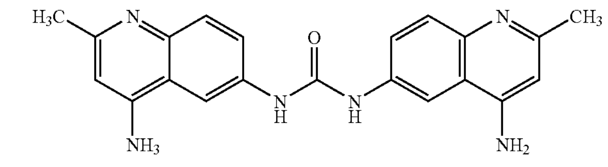 | 12155 | 95 | 0.5 ± 0.18 | Competitive |
| 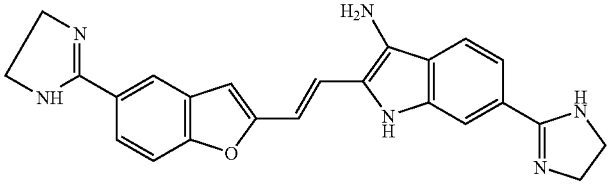 | 357756 | 90 | 4.9 ± 1.7 | Competitive |
| 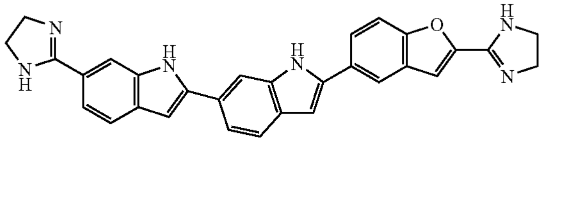 | 369718 | 90 | N.D.[a] | N.D. |

TABLE 1-continued

| Structure | NSC number | % inhibition | $K_i$ (μM) | Inhibition type |
|---|---|---|---|---|
| 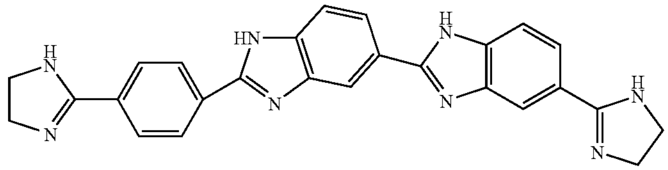 | 369721 | 90 | 4.2 ± 0.21 | Competitive |
| 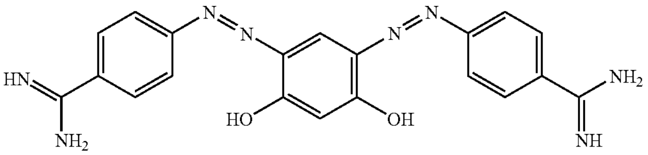 | 359465 | 48 | N.D. | N.D. |
| 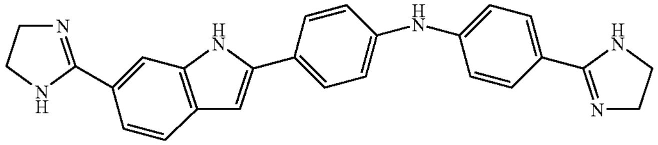 | 377362 | 33 | N.D. | N.D. |
| 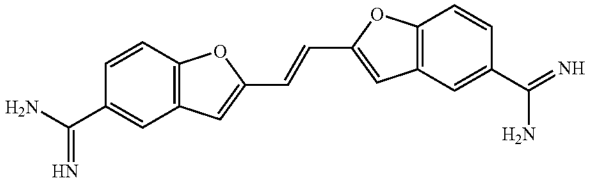 | 240899 | 0 | N.D. | N.D. |

[a]Not determined

Figure 4A:
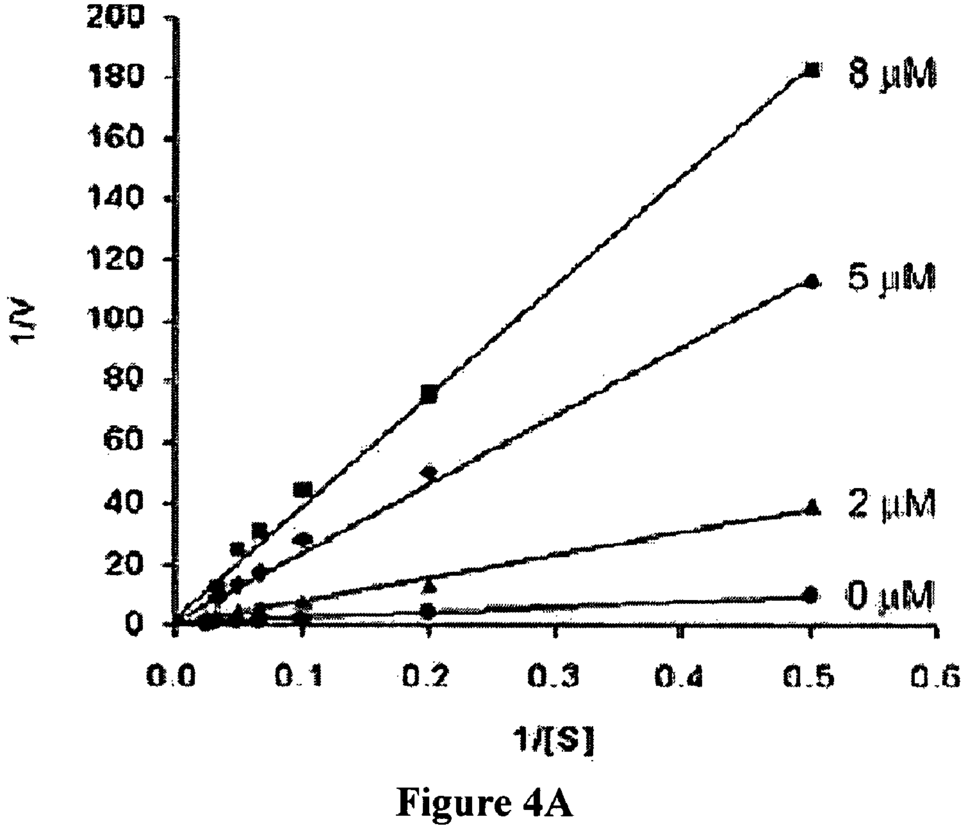
FIG. 4A shows that $K_{m(app)}$ increased with NSC 12155 concentration.
Figure 4B:
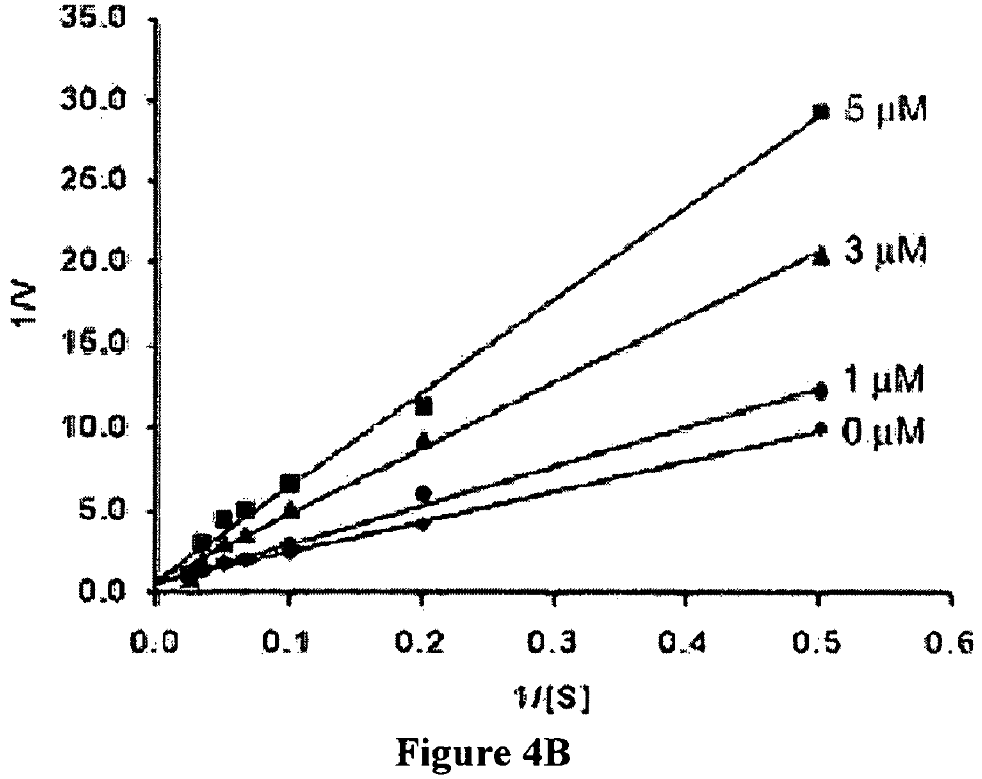
FIG. 4B shows that $K_{m(app)}$ increased with NSC 357756 concentration.
Figure 4C:
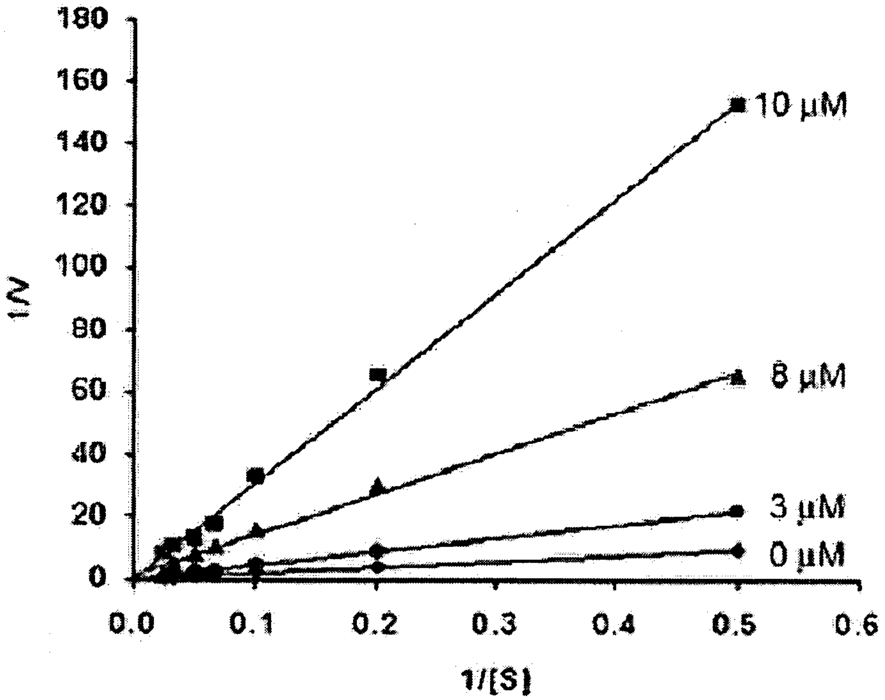
FIG. 4C shows that $K_{m(app)}$ increased with NSC 369721 concentration.

To determine the $K_i$ values and types of inhibition mediated by the inhibitors (competitive, noncompetitive or uncompetitive), the kinetic constants of the peptide substrate were determined and compared with those obtained in the presence of different inhibitor concentrations. The $K_m$ and $V_{max}$ values for the LF-catalyzed hydrolysis of the peptide substrate were 19 μM and 1.1 μmol $min^{-1}mg^{-1}$ of LF, respectively. NSC 12155, NSC 357756 and NSC 369721 showed competitive inhibition (Table 1), as they had no effect on the $V_{max}$, but $K_{m(app)}$ increased with inhibitor concentration. FIG. 4A shows that $K_{m(app)}$ increased with NSC 12155 concentration. FIG. 4B shows that $K_{m(app)}$ increased with NSC 357756 concentration. FIG. 4C shows that $K_{m(app)}$ increased with NSC 369721 concentration.

The crystal structure of LF in complex with NSC 12155 (the most potent inhibitor) was determined at a resolution of about 2.9 Å (electron density map). See FIG. 5A. NSC 12155 binds to the catalytic site of LF with its urea moiety close to the catalytic Zn atom (within about 4 Å). One quinoline ring shows strong electron density near the side chain of His 690 suggesting a favorable π-stacking interaction between the histidine's side chain imidazole and the quinoline ring. See FIG. 5B. Conversely, the second quinoline showed poor electron density, indicating that there is more rotational freedom about its quinoline-urea bond. Despite the overall lack of a strong positional preference for this quinoline, a more consistent density was detected near its amino substitution, indicating a slightly greater preference for a "C-shaped" conformation of NSC 12155 when bound to LF. This is consistent with the pharmacophoric overlap shown in FIG. 3B.

To further investigate whether the C conformation has an important role during the binding of NSC 12155 to LF, molecular docking was used to study the conformational preference of the freely rotating quinoline in the NSC 12155-LF model. Results from these analyses suggest that the NSC 12155 scaffold does prefer the planar C conformation to the "L-shaped" conformation when bound to LF. This is further supported by the following: (1) quantum mechanical calculations at the level of density functional theory, as well as analysis of related crystal structures (data not shown), support a planar preference (either L or C shaped) for NSC 12155; (2) rotation of the "free" quinoline out of plane to its planar L conformation results in unfavorable hydrophobic-polar interactions between the amino groups of NSC 12155 and the side chain of Val 675; (3) in the planar C conformation, the urea oxo and quinoline amino substituents of NSC 12155 are more likely to engage in favorable intramolecular acid-base interactions; (4) molecular docking studies of 32 substituted quinoline and urea derivatives (chemoinformatically mined from the NCI repository), which were inactive in the LF assay (data not shown), indicate that these scaffolds are either incapable of forming the preferred C conformation of NSC 12155 or lack features that would enable favorable binding; and (5) additional modeling studies of NSC 12155 indicate that the urea nitrogens are within range to form favorable acid-base interactions with the carboxylate of Glu 687 (supported by X-ray data: distances of the urea nitrogens of NSC 12155 are 4.12 Å and 4.72 Å from OE1 and OE2 of Glu 687, respectively).

To determine the ability of the small molecule inhibitors to protect macrophages against LF, the cells were pretreated with NSC 12155, NSC 357756, NSC 369718 or NSC 369721 at concentrations ranging from about 1 to about 100 μM and further incubated in the presence of anthrax lethal toxin. Cell viability was determined using MTT dye. See FIG. 6. NSC 357756 showed about 96% protection at 100 μM, whereas NSC 12155 and NSC 369718, the most potent of the LF inhibitors in vitro, showed lower protection at about 100 μM. These three compounds showed some protection less than about 25 μM suggesting that they might be good leads against lethal toxin in vivo. Additionally, NSC 369721 was ineffective even at 100 μM in the cell-based toxicity assay. The moderate protection of these inhibitors is probably attributable to their limited ability to penetrate the macrophage cell membrane. The cell-based data may be used to develop second-generation LF inhibitors.

Molecular docking studies of both inactive and active analogs of the compounds shown in Table 1 are consistent with the pharmacophore of the present invention. For example, the amidine groups of NSC 240899 formed unfavorable steric and polar interactions when docked in the NSC 12155-binding site which may explain this compound's complete lack of LF inhibition despite its structural similarity to NSC 357756. NSC 357756, NSC 369718 and NSC 369721 did not engage in unfavorable interactions when docked in the NSC 12155-binding site, supporting this hypothesis. However, the large size and solvent-exposed nature of the LF-binding groove also allows NSC 357756, NSC 369718 and NSC 369721 to assume several different binding modes near the enzyme's active site.

The X-ray structure of the LF-NSC 12155 complex and the extensive molecular docking studies with LF inhibitors also allow for the identification of favorable structural modifications that may enhance the potency of these compounds. For example, X-ray and molecular modeling studies of NSC 12155 indicate that the 0.5-μM $K_i$ of this inhibitor could be improved by replacing one of the quinoline moieties with a pyrrole. Such a modification would provide an additional hydrogen bond with the carboxylate of Glu 687. The planar C conformation of NSC 12155 could be stabilized by replacing its amino substituents with nitro groups, thus facilitating resonance throughout this scaffold. Additionally, these results in concert with Turk et al. suggests that replacement of one of NSC 12155's quinoline rings with a tetra-aza-benzo(a)fluorene would enhance binding by placing additional molecular volume in the S1' site of LF. See Turk, B. E. et al. (2004) Nat. Struct. Mol. Biol. 11(1):60-66, which is herein incorporated by reference. Moreover, the deep S1' pocket (visible in FIG. 3A, next to zinc) seems highly selective, such that a large hydrophobic ring structure would probably increase the affinity of an inhibitor for the LF active site.

As provided herein, the present invention provides a pharmacophore model and small molecules that inhibit anthrax lethal factor protease activity. These small molecules and other compounds that fit the pharmacophore model may be used in therapies and compositions for treating, inhibiting, or preventing toxicity to anthrax lethal factor protease. These small molecules and other compounds that fit the pharmacophore model may be used in therapies and compositions for treating a subject exposed to *Bacillus anthracis,* anthrax lethal factor protease, or both. These small molecules and other compounds fitting the pharmacophore model of the present invention may be modified according to methods known in the art to increase inhibitor bioavailability while at the same time allowing for optimal binding affinity in the LF substrate-binding cleft.

CATALYST® software allows mapping of all functions generated in a pharmacophore to the more potent analogues and fewer or none in the less potent analogues of the training set through conformational energy and best-fit scoring calculations. The technique involves a 3D screening of all the conformations of the molecule by matching the pharmacophore features. See Kurogi, Y and Gunner, O F (2001) Current Medicinal Chemistry 8:1035-1055, which is herein incorporated by reference.

Although CATALYST® 4.7 software (Accelrys Inc., San Diego, Calif.) may be used for 3D QSAR analysis and pharmacophore generation, other methods known in the art such as those described in PHARMACOPHORE PERCEPTION, DEVELOPMENT, AND USE IN DRUG DESIGN (2000) Ed. Osman F. Gunner, International University Line, La Jolla, Calif., may be used according to the present invention.

As disclosed herein, molecular modeling software, CATALYST® 4.7 software (Accelrys Inc., San Diego, Calif.) may used to construct a three-dimensional QSAR pharmacophore model for the inhibitory activities exhibited by some inhibitor compounds known in the art. A training set of comprising the small molecule inhibitors disclosed herein may be used to construct a 3D QSAR pharmacophore model. Although more or less compounds in the training set may be used, in preferred embodiments, about 10 to about 20 chemically diverse molecules with biological activity covering 4 to 5 orders of magnitude for the training set are preferred.

The structures of the training set may be either imported into or edited within CATALYST® by assembling the structural fragments and energy minimized to the closest local minimum using the CHARMM-like force field. Molecular flexibility may be taken into account by considering each compound as an ensemble of conformers representing different accessible areas in a three dimensional space. The "best searching procedure" may be applied to select representative conformers within about 20 kcal/mol above the calculated global minimum. See Grigorov, M, et al. (1995) J. Chem. Inf. Comput. Sci. 35:285-304, which is herein incorporated by reference.

Hypothesis generation may be carried out with the training set by methods known in the art. See Greenridge, P A and J. Weiser (2001) Mini Reviews in Medicinal Chemistry 1:79-87; Grigorov, M, et al. (1995) J. Chem. Inf. Comput. Sci. 35:285-304; which are herein incorporated by reference. The coordinates of a pharmacophore model are dependent upon the particular coordinate system used, and those skilled in the art will recognize that, although rotation and translation of these coordinates may change the specific values of these coordinates, they will in fact define the pharmacophore model of the present invention. The pharmacophore model of the present invention is intended to encompass any model, after optimal superposition of the models, comprising the identified features and having a root mean square of equivalent features of less than about 3.0 Å. More preferably, the pharmacophore model of the present invention encompasses any model comprising the features identified herein and having a root mean square of equivalent features of less than about 1.5 Å, even more preferably, less than about 1.0 Å, and most preferably less than about 0.5 Å.

As those of skill in the art will readily recognize, chemically different substructures can present certain identical three-dimensional space-filling features, and accordingly, the models of the present invention comprise features that may or may not correspond to actual functional groups in any given compound. Additionally, since compounds having different structural formulas may have the same or similar pharmacophore hypotheses, the compounds of the present invention are not limited to compounds having similar chemical structures.

As provided herein, the pharmacophore model may be cross-validated by using a test set of compounds known in the art. The test set compounds may be screened for the ability to inhibit anthrax lethal factor protease activity by the assays provided herein or other methods known in the art and then compared with the activity of those compounds in the original training set. The validity of the pharmacophore model to other compounds found to inhibit anthrax lethal factor protease activity may be examined. The pharmacophore features may be mapped onto the compounds and should be found to map significantly well with known compounds to varying degrees.

There are 3 parameters such as the "best-score fit", estimate of activity, and conformational energy costs are involved in the present case to assess the quality of the pharmacophore mapping. The mapping of a pharmacophore on the three-dimensional structure of a compound is carried out by means of a few calculations. The compound to be mapped to a pharmacophore is converted to a three-dimensional configuration and all its conformations with energies are stored in a computer which then performs the analytical calculations which compares the three-dimensional conformers of the compound being mapped and the pharmacophore. Perfect mapping means that the features of the pharmacophore match exactly with at least one of the conformers of the compound. "Best-fit scores" indicate the degree of matching, conformational energy indicates how much of energy would be spent by the molecule to match the pharmacophore, and estimate of activity is the prediction of activity should the compound be a member of the training set from the pharmacophore was originally developed.

The pharmacophore model of the present invention may be used to search three-dimensional multiconformer databases and other chemical databases, including an in-house Chemical Information System (Chemical Information System, Division of Experimental Therapeutics, Walter Reed Army Institute of Research, Silver Spring, Md.), National Cancer Institute, IBS and Maybridge databases, to screen for compounds that inhibit anthrax lethal factor protease activity. A chemical database may be transformed into a multiconformer database in CATALYST® using the catDB® utility program as implemented in the software. The catDB® format allows a molecule to be represented by a limited set of conformations thereby permitting conformational flexibility to be included during the search of the database.

The pharmacophore models of the present invention can be used to evaluate inhibitory activity and potency of a candidate compound. The candidate compounds being evaluated may be designed de novo using the models of the invention, or alternatively, be a compound, e.g., chosen from a library of compounds. Using the pharmacophore model of the invention and the methods of identification disclosed herein, one may predict the activity of a candidate compound based upon its fit with the pharmacophore model of the invention. Further, one may even predict the relative degree of activity via the methods of the invention by calculation of the $K_1$ (apparent) value for a compound.

After identifying a candidate compound to be evaluated for the ability to inhibit anthrax lethal factor protease activity, the three-dimensional structure of the compound may be determined. This may already have been done if, e.g., the compound was obtained from a structural database wherein three-dimensional x, y and z coordinates were used to define the compound. Alternatively, the three-dimensional structures of small molecules can be readily determined by methods known to those of skill in the art, including but not limited to, X-ray crystallography, nuclear magnetic resonance spectrometry, and the like. The structures obtained from structural databases are usually the structures of compounds alone, uncomplexed with other molecules. If the three-dimensional structure is not known, one may use computer programs, such as CATALYST®, to predict the three-dimensional structure of the compound. Three-dimensional conformers may be generated from a starting structure using methods well known in the art such as the Best or Fast Conformational Analyses (Molecular Simulations, Inc., San Diego, Calif.) with an energy set to a range of 0 to 50 Kcal/mol, preferably 0 to 35 Kcal/mole, and most preferably 0 to 10 Kcal/mole, and the maximum number of conformations set to 100, preferably 175, and most preferably 255. The pharmacophore model may be then compared to a given compound using tools to compare the structural features of each, such as COMPARE™ within the VIEW HYPOTHESIS™ workbench (Molecular Simulations, Inc., San Diego, Calif.).

The degree of fit of a particular compound structure to the pharmacophore model may be calculated by determining, using computer methods, if the compound possesses the chemical features of the model and if the features can adopt the necessary three-dimensional arrangement to fit the model. The modeling program will indicate those features in the model having a fit with the particular compound.

In preferred embodiments, the present invention encompasses compounds that exhibit the ability to inhibit anthrax lethal factor protease activity and map well to the pharmacophore model disclosed herein. For example, methods for suitably superimposing compounds on a three-dimensional representation of the pharmacophore model of the present invention using computational methods is well known to those of skill in the art. A superposition of structures and the pharmacophore model is defined as a minimization of the root mean square distances between the centroids of the corresponding features of the molecule and the pharmacophore. A Van der Waals surface is then calculated around the superimposed structures using a computer program such as CERIUS™ (Molecular Simulations, Inc., San Diego, Calif.).

The compounds of the present invention may be made according to methods known in the art.

In accordance with a convention used in the art, ⨯and "-" as, for example, in "—R" are used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl" is intended to mean a non-aromatic monovalent monocyclic, bicyclic, or tricyclic radical comprising 3-14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

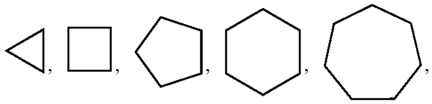
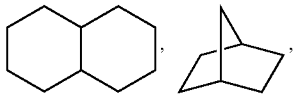
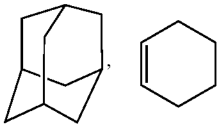
, and
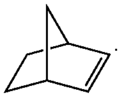

A "heterocycloalkyl" is intended to mean a non-aromatic monovalent monocyclic, bicyclic, or tricyclic radical, which is saturated or unsaturated, comprising 3-18 ring members, which includes 1-5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

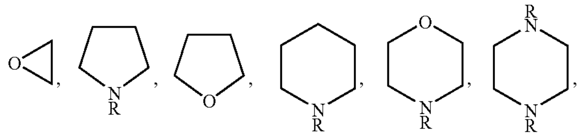
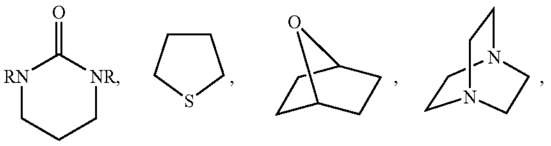
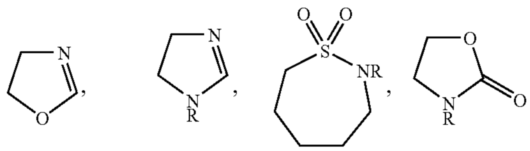
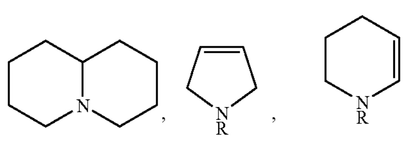
, and
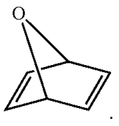

An "aryl" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

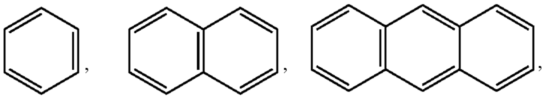
, and
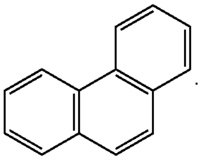

A "heteroaryl" is intended to mean an aromatic monovalent monocyclic, bicyclic, or tricyclic radical comprising 4-18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

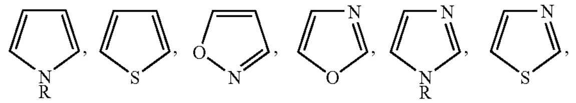
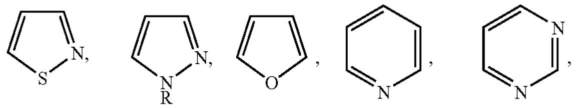
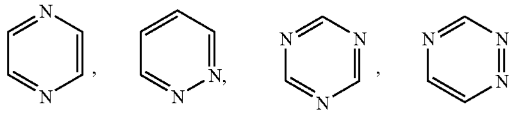
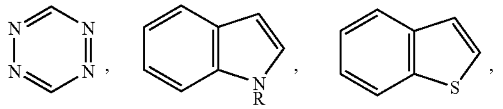
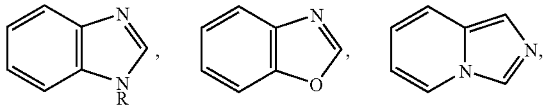
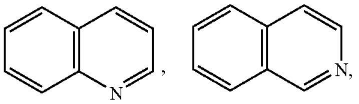
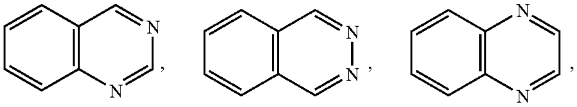
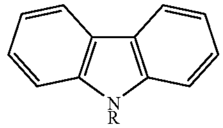
,
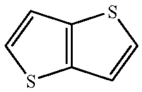
, and
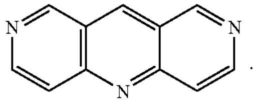

A "heterocycle" is intended to mean a heteroaryl or heterocycloalkyl group (each of which, as defined above, are optionally substituted).

The terms “aryl” (Ar) and “heteroaryl” refer to monocyclic and polycyclic unsaturated or aromatic ring structures, with “aryl” referring to those that are carbocycles and “heteroaryl” referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An “acyl” is intended to mean a —C(O)—$R^a$ radical, where $R^a$ is a suitable substituent as defined below.

A “thioacyl” is intended to mean a —C(S)—$R^a$ radical, where $R^a$ is a suitable substituent as defined below.

A “sulfonyl” is intended to mean a —$SO_2R^a$ radical, where $R^a$ is a suitable substituent as defined below.

A “hydroxyl” is intended to mean the radical —OH.

An “amino” is intended to mean the radical —$NH_2$.

An “alkylamino” is intended to mean the radical —$NHR^a$, where $R^a$ is an alkyl group.

A “dialkylamino” is intended to mean the radical —$NR^aR^b$, where $R^a$ and $R^b$ are each independently an alkyl group.

An “alkoxyl” is intended to mean the radical —$OR^a$, where $R^a$ is an alkyl group. Exemplary alkoxyl groups include methoxyl, ethoxyl, propoxyl, and the like.

An “alkoxycarbonyl” is intended to mean the radical —C(O)$OR^a$, where $R^a$ is an alkyl group.

An “alkylsulfonyl” is intended to mean the radical —$SO_2R^a$, where $R^a$ is an alkyl group.

An “alkylaminocarbonyl” is intended to mean the radical —C(O)$NHR^a$, where $R^a$ is an alkyl group.

A “dialkylaminocarbonyl” is intended to mean the radical —C(O)$NR^aR^b$, where $R^a$ and $R^b$ are each independently an alkyl group.

A “mercapto” is intended to mean the radical —SH.

An “alkylthio” is intended to mean the radical —$SR^a$, where $R^a$ is an alkyl group.

A “carboxyl” is intended to mean the radical —C(O)OH.

A “carbamoyl” is intended to mean the radical —C(O)$NH_2$.

An “aryloxyl” is intended to mean the radical —$OR^c$, where $R^c$ is an aryl group.

A “heteroaryloxyl” is intended to mean the radical —$OR^d$, where $R^d$ is a heteroaryl group.

An “arylthio” is intended to mean the radical —$SR^c$, where $R^c$ is an aryl group.

A “heteroarylthio” is intended to mean the radical —$SR^d$, where $R^d$ is a heteroaryl group.

A “leaving group” (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A “protecting group” is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, 3rd edition, John Wiley and Sons, New York, N.Y. (1999).

The term “suitable organic moiety” is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be “optionally substituted” by one or more suitable “substituents”. The term “substituent” or “suitable substituent” is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term “optionally substituted” is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the compounds of the present invention, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See e.g. Lee, et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin), peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See e.g., Bertolini, G, et al., (1997) J. Med. Chem. 40:2011-2016; Shan, D, et al., *J. Pharm. Sci.,* 86(7):765-767; Bagshawe K (1995) Drug Dev. Res. 34:220-230; Bodor, N (1984) Advances in Drug Res. 13:224-331; Bundgaard, H *Design of Prodrugs* (Elsevier Press, 1985); and Larsen, I. K., *Design and Application of Prodrugs*, Drug Design and Development (Krogsgaard-Larsen et al., eds., Harwood Academic Publishers, 1991).

If the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the present invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the compound of the present invention and salts may exist in different crystal or polymorphic forms, all of which are intended to be within the scope of the present invention and specified structural formulas.

The specification for the dosage unit forms of the invention are dictated by and directly dependent on the unique characteristics of the active compound and the limitations inherent in the art of compounding such an active compound for the treatment of individuals. In general, formulations containing greater concentrations of active ingredient provide more effective and long-lasting protection.

A compound of the present invention may be administered in an effective amount to a mammal such as a human. An "effective amount" is intended to mean that amount of a given compound that is sufficient to inhibit anthrax lethal factor protease activity as compared to a control. The amount of a given compound of the present invention that will correspond to such an amount will vary depending upon factors such as the given compound, the pharmaceutical or cosmetic formulation and route of administration, and the like, but can nevertheless be routinely determined by one skilled in the art. An "effective amount" of a compound of the present invention may be readily determined by one of ordinary skill by routine methods known in the art. As used herein, an "effective amount" refers to an amount that provides an observable desired change as compared with a control. For example, if the desired change is a given inhibition of a given protein and administration of 0.9 μM of a compound does not produce an observable inhibition as compared with a control, but the administration of 1 μM does produce an observable inhibition, then the effective amount is about 1 μM or more.

A therapeutically effective amount may be readily determined by standard methods known in the art. As defined herein, a therapeutically effective amount of a compound of the invention ranges from about 0.1 to about 25.0 mg/kg body weight, preferably about 1.0 to about 20.0 mg/kg body weight, and more preferably about 10.0 to about 20.0 mg/kg body weight. Preferred topical concentrations include about 0.1% to about 20.0% in a formulated salve.

The skilled artisan will appreciate that certain factors may influence the dosage required to effectively treat a subject, including but not limited to the severity of toxicity and exposure, previous treatments, the general health and/or age of the subject, and other diseases present. Moreover, treatment of a subject with a therapeutically effective amount of the compound can include a single treatment or, preferably, can include a series of treatments.

Methods for treating toxicity and exposure to anthrax lethal factor according to the present invention may consist of a single administration of a least one compound of the present invention, or alternatively comprise a series of administrations. For example, a subject may be treated with a compound of the present invention at least once. However, the subject may treated with the compound from about one time per week to about once daily or multiple times daily for a given treatment period. The length of the treatment period will depend on a variety of factors that may be readily determined by one skilled in the art.

In a preferred example, a subject is treated with a compound of the invention in the range of between about 0.1 to about 25.0 mg/kg body weight, at least one time per week for between about 5 to about 8 weeks, and preferably between about 1 to about 2 weeks. It will also be appreciated that the effective dosage of the compound used for treatment may increase or decrease over the course of a particular treatment. Changes in dosage may result and become apparent by standard diagnostic assays known in the art. In some conditions chronic administration may be required.

The pharmaceutical and cosmetic formulations of the invention comprise at least one compound of the present invention and may be prepared in a unit-dosage form appropriate for the desired mode of administration. The pharmaceutical formulations of the present invention may be administered by any suitable route including oral, rectal, nasal, topical (including buccal and sublingual), vaginal and parenteral (including subcutaneous, intramuscular, intravenous and intradermal). In some embodiments, the compounds of the present invention are topically administered to a subject.

The formulations of the present invention comprise an effective amount of at least one compound of the present invention, and an inert, pharmaceutically or cosmetically acceptable carrier or diluent. As used herein the language "pharmaceutically or cosmetically acceptable carrier" is intended to include any and all solvents, dispersion media, coatings, antibacterial and antifungal agents, isotonic and absorption delaying agents, and the like, compatible with pharmaceutical or cosmetic administration. The pharmaceutical or cosmetic carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically or cosmetically active substances is well known in the art.

Except insofar as any conventional media or agent is incompatible with the active compound, use thereof in the formulation is contemplated. Supplementary active compounds can also be incorporated into the formulations. Supplementary active compounds include antibiotics, antiprotozoal agents, antifungal agents, and antiproliferative agents known in the art, analgesics and other compounds commonly used to treat diseases and disorders associated with given pests to be repelled.

Antibiotics include penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, kirromycin, thiostrepton, micrococcin, fusidic acid, thiolactomycin, fosmidomycin, and the like.

Antiprotozoal agents include chloroquine, doxycycline, mefloquine, metronidazole, eplomithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like.

Antifungal agents include amphotericin B, fluconazole, itraconazole, ketoconazole, potassium iodide, flucytosine, and the like.

Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemicitabine, gemtuzumab-ozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, steroids, and the like.

Supplementary compounds also include antidotes known in the art such as botulism antitoxin, tetanus antitoxin, diphtheria antitoxin, and the like.

The formulations of the invention may be manufactured in manners generally known for preparing pharmaceutical and cosmetic compositions, e.g., using conventional techniques such as mixing, dissolving, granulating, dragee-making, levigating, emulsifying, encapsulating, entrapping or lyophilizing. The formulations may be formulated in a conventional manner using one or more physiologically acceptable carriers, which may be selected from excipients and auxiliaries that facilitate processing of the active compounds into preparations which can be used pharmaceutically or cosmetically.

For topical formulations of the present invention, pharmaceutically acceptable excipients or cosmetically acceptable carriers and additives include solvents, emollients, humectants, preservatives, emulsifiers, pH agents, and the like. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, face paints, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art. The compounds of the present invention may be in powder form for constitution with a suitable vehicle, e.g., sterile pyrogen-free water, before use. The formulations of the present invention may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

In some embodiments, a compound of the present invention is prepared with a carrier that will prolong the activity of the compound such as a controlled release formulation, prevent or inhibit degradation or loss of activity, or prevent or inhibit loss of the compound due to factors such as metabolism. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically or cosmetically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from the cell culture assays and animal studies can be used in formulating a range of dosage for human use according to methods known in the art.

The following Examples are intended to illustrate, but not to limit the present invention.

The compounds used in the following examples are as follows: The NCI Diversity set was obtained in 96-well plate format from the National Cancer Institute. See the World Wide Web at dtp.nci.nih.gov/branches/dscb/diversity_explanation.html, which is herein incorporated by reference.

EXAMPLE 1

High Throughput Assay of Anthrax LF Activity

A. Fluorescent Plate-Based Assay

For high-throughput screening in 96-well plates, the reaction volume was 100 μL per well. Master mix containing 40 mM HEPES, pH 7.2, 0.05% (v/v) Tween 20, 100 μM CaCl; and 1 μg $ml^{-1}$ of LP was added to each well containing 100 μM of NCI Diversity Set compound. The reaction was initiated by adding the optimized peptide with a fluorogenic coumarin group at the N terminus and a 2,4-dinitrophenyl (dnp) quenching group at the C terminus, to a final concentration of 20 μM as provided in The color version of this figure may be found in Panchal, et al. (2004) Nature Struct. & Molec. Biol. 11:67-72, which is herein incorporated by reference. Kinetic measurements were obtained every minute for 30 minutes using a fluorescent plate reader (Molecular Devices, Gemini XS). Excitation and emission maxima were 324 nm and 395 nm, respectively.

B. HPLC-Based Assay

An HPLC-based assay was used to validate the hits from the primary screen and eliminate the false positives obtained owing to fluorescence quenching. Reaction mix (30 μl total volume) containing 40 mM HEPES, pH 7.2, 0.05% (v/v) Tween 20, 100 μl $CaCl_2$ LF substrate (20 μM final concentration), with or without the inhibitor (20 μM final concentration), was incubated with LF (1 μg $ml^{-1}$) for 30 minutes at 30° C. The reaction was stopped by adding 8 M guanidine hydrochloride in 0.3% (v/v) TFA.

Substrate and products were separated on a Hi-Pore C18 column (Bio-Rad) using 0.1% (v/v) TFA (solvent A) and 0.1% (v/v) TFA+70% (v/v) acetonitrile (solvent B). The column effluent was monitored at 365 nm, where the substrate and C-terminal cleavage products showed greater absorbance.

The HPLC-based assay was used for enzyme kinetic studies. Kinetic constants were obtained from plots of initial rates with seven concentrations of the substrate. For the best inhibitors, $K_i$ and the type of inhibition were evaluated using seven different concentrations of the substrate ranging from about 2 to about 40 μM and four different concentrations of the inhibitor. $K_i$ values for the competitive inhibitors were calculated using the equation $K_i=[I]/[(K_{m(app)}/K_m)-1]$, where [I] is the inhibitor concentration. See Segel, I. H. (1975) ENZYME KINETICS Wiley, New York, which is herein incorporated by reference. $K_i$ values in Table 1 are the averages ±s.d.

EXAMPLE 2

LF Refinement and Inhibitor Docking

The structure of LF was energy-refined using the Discover (Accelrys Inc. San Diego, Calif.) program's cff91 force field. The strategy used herein entailed using a step-down, template forced minimization procedure with the Zn coordination site fixed. During the refinement, the zinc ion, and residues coordinating the zinc ion, were fixed in their original coordinates. The strategy entailed applying 2,000 kcal/mol per $Å^2$ of force that was stepped off the structure in 100-kcal/mol decrements by minimizing with conjugate gradients, until the norm of the gradient was 0.01 kcal/Å. See Giannakakou, et al. (2000) PNAS 97:2904-2909, which is herein incorporated by reference. This process was repeated until all applied external force was removed. The resulting coordinates of the final model were within the experimentally determined x-ray crystallographic resolution.

Using InsightII molecular modeling software (Accelrys, Inc., San Diego, Calif.), identified inhibitors were manually docked into the substrate binding cleft, and Van der Waals violations of 0.25 Å were removed by small adjustments to side-chain torsion angles and inhibitor positioning. The inhibitor-enzyme structure coordinates were subsequently tether minimized in the same manner as described above, and the final structure was subjected to hydropathic analysis using the program HINT (eduSoft, Richmond, Va.).

EXAMPLE 3

Conformer Generation

Conformational models of inhibitors were generated using Catalyst 4.7® software (Accelrys, Inc., San Diego, Calif.). Inhibitors were imported into Catalyst® and energy minimized to the closest local minimum using the generalized CHARMM-like force field, as implemented in the program. Following, the "best quality" conformational search option was employed to generate conformers within 20 kcal $mol^{-1}$ from the global energy minimum.

EXAMPLE 4

Data Mining

Catalyst 4.7 (Accelrys, Inc., San Diego, Calif.) was used for all database mining. Briefly, the imidazoline rings of NSC 357756 were used to form a three-dimensional search query (A.R.H. et al., unpublished data). Subsequent molecular docking studies (see above) were used to suggest candidates for biological testing.

EXAMPLE 5

Quantum Mechanical Calculations

The conformations (L and C shaped) of NSC 12155 were fully optimized (until the norm of the gradient was less than about $5.0\times10^4$) using DGauss (Oxford Molecular Group). Local spin density (LSD) correlation potentials were approximated by the Vosko-Wilk-Nusair method known in the art and gaussian analytical functions were used as basis sets. LSD-optimized orbital basis sets of double ζ-split valence polarization quality were used. See Vosko, S. J., et al. (1980) Can. J. Phys. 58:1200-1211; and Godbout, N., et al. (1992) Can. J. Chem. 70:560-571, which are herein incorporated by reference. In final optimizations, the BLYP exchange-correlation functional was applied as a nonlocal gradient correction after each self-consistent field cycle. See Becke, A. D. (1993) J. Chem. Phys. 98:5648-5652; and Lee, C., et al. (1998) Phys. Rev. B Condens. Matter 37:785-789, which are herein incorporated by reference.

EXAMPLE 6

Crystallization

Native, wild-type LF protein was crystallized using 13 mg $ml^{-1}$ LF. Crystals were grown from 1.7 M $(NH_4)_2SO_4$, 0.2 M Tris-HCl, pH 7.5-8.0, 2 mM EDTA, using hanging-drop vapor diffusion. See Pannifer, A. D. et al. (2001) Nature 414:229-233, which is herein incorporated by reference. Monoclinic crystals appeared after four days to two weeks, and were then harvested for experiments. The LF crystals belong to the monoclinic space group $P2_1$, with unit cell dimensions a=96.70 A, b=137.40 A, c=98.30 A, a=γ=90°, β=98°, containing two molecules per asymmetric unit.

EXAMPLE 7

LF-Inhibitor Complexes

LF native crystals were harvested from the hanging drops in which they were grown, bathed in several rounds of fresh buffer without EDTA containing 1.9 M $(NH_4)_2SO_4$, 0.2 M Tris-HCl, pH 8.0, and left to soak in this solution for a further 30 minutes. These crystals were then used to obtain the protein-inhibitor-zinc complexes. All manipulations were done at room temperature (about 23 to about 26° C.).

The LF-NSC 12155-Zn complex was obtained by soaking an individual native LF monoclinic $P2_1$ crystal in a solution of 1 mM $ZnSO_4$, 1.9 M $(NH_4)SO_4$, 0.2 M Tris-HCl, pH 8.0 for 5 minutes. The crystal was then transferred to a solution of 1.0 mM NSC 12155, 1% (v/v) DMSO, 1.9 M $(NH_4)SO_4$, 0.2 M Tris-HCl, pH 8.0 for 15 minutes. Finally, the crystal was transferred into a cryoprotectant solution of 1.0 mM NSC 12155. 2.4 M $(NH_4)_2SO_4$, 0.2 M Tris-HCl, pH 8.0, 2 mM EDTA, 25% (v/v) glycerol and soaked at room temperature for 1 minute. The crystal was then immediately mounted onto a cryoloop and flash-frozen in liquid nitrogen. All data were collected at 100 K.

EXAMPLE 8

Data Collection

Datasets for the LF complexes were collected at the Stanford Synchrotron Radiation Laboratory (SSRL, Menio Park, Calif.) on beamline 9-1 (wavelength=0.983 A). X-ray diffraction data were collected for the LF-NSC 12155-Zn complex to a resolution limit of 2.90 Å. Data collection statistics are shown in Table 2 as follows:

TABLE 2

Data Collection Summary of LF-NSC 12155-Zn Complex Crystal

| | |
|---|---|
| Resolution range (Å) | 25.0-2.90 |
| Reflections | |
| Total | 175.849 |
| Unique | 56.384 |
| Completeness (%)[1] | 99.5 (99.3) |
| $R_{sym}$ (%)[1,2] | 10.6 (49.8) |
| I/σ I[1] | 11.7 (2.9) |

[1]Values in parentheses are for the highest resolution shell

[2]$R_{sym} = \Sigma|I - \langle I\rangle|/\Sigma\langle I\rangle$, where I is the observed intensity and <I> is the average intensity from multiple observations of symmetry-related reflections.

EXAMPLE 9

Structure Solution and Refinement

Collected data were processed in the HKL package using methods known in the art. See Otwinowski, Z. & Minor, W. (1997) Methods Enzymol. 276:307-326, which is herein incorporated by reference. Refinement and model building were done in CNS and O, respectively, using methods known in the art. See Brunger, A. T. et al. (1998) Acta Crystallogr. 054:905-921; and Jones, T. A., et al. (1991) Acta Crystallogr. A 47:110-119, which is herein incorporated by reference. Using PDB entry 1J7N as the starting model, the model of LF alone was put through rigid body refinement and then minimization before the first initial maps were calculated for model building and further refinement. Excess electron density at 1.0σ indicated the binding location of the inhibitor in the active site of LF. The model of the inhibitor was then built into this position and further refined in CNS. See Brunger, A. T. et al. (1998) Acta Crystallogr. 054:905-921, which is herein incorporated by reference. The final R-factors were $R_{free}$=27.58% and $R_{work}$=22.38%. The final model falls within or exceeds the limits of all the quality criteria of PROCHECK from the CCP4 suite. See The CCP4 suite: programs for protein crystallography (1994) Acta Crystallogr. D. 50:760-763, which is herein incorporated by reference.

The coordinates and structure factors for the LF-NSC 12155-Zn complex have been deposited in the Protein Data Bank (accession code 1PWP), and are herein incorporated by reference.

EXAMPLE 10

Cytotoxicity Assay

J774A.1 cells were preincubated with DMSO control or compounds for 30 minutes and then treated with PA (50 ng $ml^{-1}$) and LF (14 ng $ml^{-1}$). After a 4 hour incubation with the toxin, 25 μl of MTT (1 mg $ml^{-1}$) dye was added and the cells were further incubated for 2 hours. The reaction was stopped by adding an equal volume of lysis buffer (20% (v/v) DMF and 20% (w/v) SDS, pH 4.7). Plates were incubated overnight at 37° C. and absorbance was read at 570 nm in a multiwell plate reader. Experiments were done in duplicate and repeated three independent times for each of the inhibitors tested. The results shown in FIG. 6 are the average±s.d.

EXAMPLE 11

3D-QSAR & Pharmacophore Generation

The molecular modeling software, CATALYST® 4.7 software (Accelrys Inc., San Diego, Calif.) is used to construct a three-dimensional QSAR pharmacophore model for the activities exhibited by compounds that inhibit anthrax lethal factor protease activity. A training set is used to construct the pharmacophore model.

The pharmacophore model is developed by placing suitable constraints on the number of available features such as, aromatic hydrophobic or aliphatic hydrophobic interactions, hydrogen bond donors, hydrogen bond acceptors, hydrogen bond acceptors (lipid), and ring aromatic sites to describe the activity of the compounds.

During this pharmacophore or hypothesis generation, the molecules are mapped to the features with their pre-determined conformations generated earlier using the "fast fit" techniques in the CATALYST®.

EXAMPLE 12

Cross Validation of Pharmacophore Model

The pharmacophore model may be cross-validated by generating a test set of different inhibitory compounds known in the art. The test set compounds may be screened for inhibitory activity in a manner identical to the compounds of the original training set according to Example 1 or methods known in the art. The compounds of the test set for cross validation should not be ones of the original training set used for automatic generation of the pharmacophore.

Regression analysis is performed by mapping this test set onto the features of the pharmacophore and should show remarkable consistency of the model (R greater than about 0.85, preferably greater than about 0.90, more preferably greater than about 0.95). Regression information is used to estimate activity of the training set of the compounds as well as to estimate the unknown compounds. The greater the fit of the pharmacophore with the compound, the more likely the compound will exhibit inhibitory activity. The regression for both the training set and the test set is calculated by the following equation:

$$-\log(\text{activity})_{Est}=\text{Fit}*\text{Slope}+Y\text{ intercept}$$

See Catalyst® Tutorials, Release 4.5, August 1999, Accelrys Scientific Support. 9685 Scranton Road, San Diego, Calif. 92121-3752, which is herein incorporated by reference.
Table 3 shows compounds identified as fitting the pharmacophore model of the present invention and percent inhibition of anthrax lethal factor protease.
TABLE 3
| Structure | NSC Number | Percent Inhibition |
|---|---|---|
| 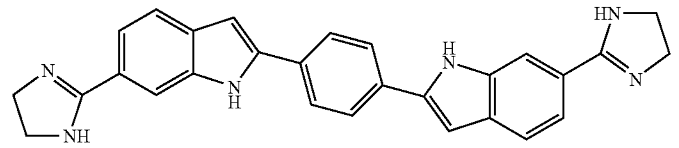 | 317881 | 97 |
| 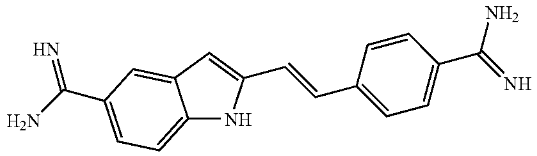 | 317884 | 95 |
| 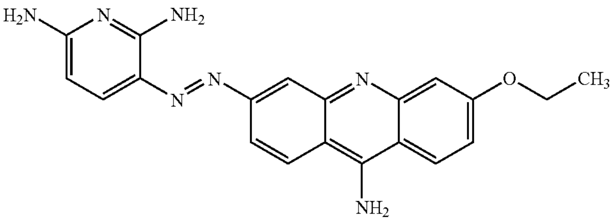 | 354961 | 95 |
| 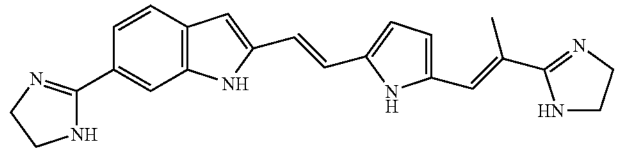 | 317880 | 93 |
| 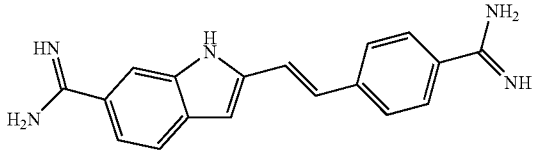 | 317886 | 93 |
| 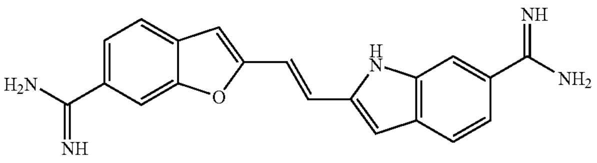 | 294200 | 92 |
| 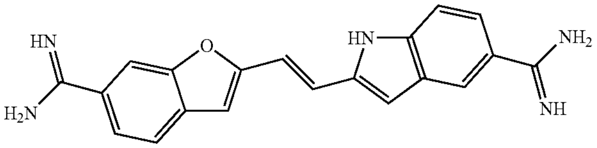 | 294203 | 92 |

TABLE 3-continued
| Structure | NSC Number | Percent Inhibition |
|---|---|---|
| 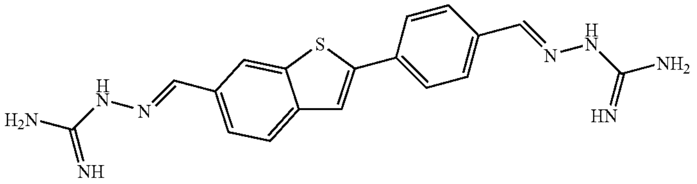 | 341909 | 90 |
| 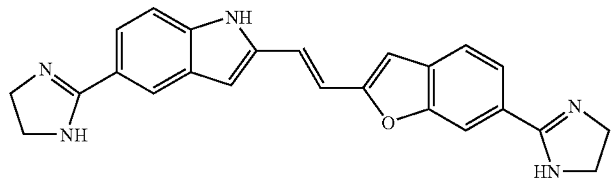 | 294201 | 88 |
| 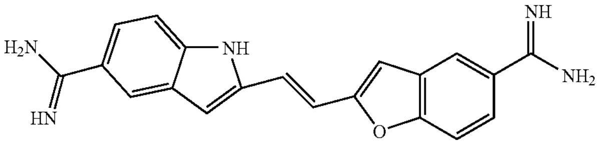 | 290107 | 85 |
| 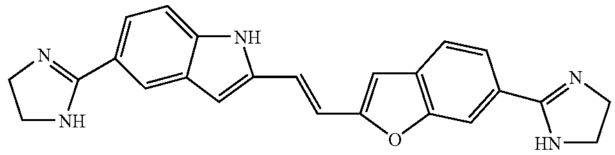 | 294204 | 84 |
| 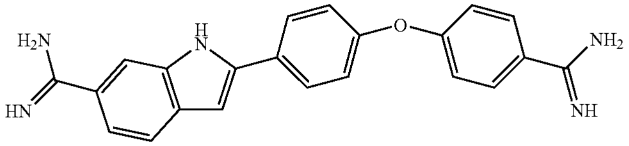 | 240898 | 72 |
| 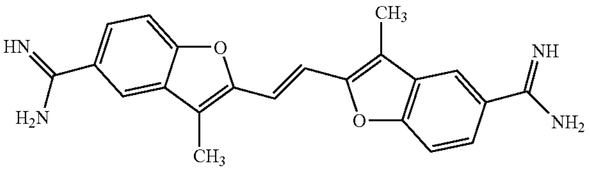 | 266474 | 71 |
| 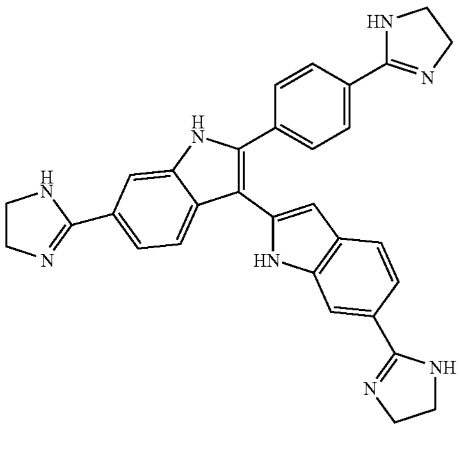 | 341911 | 64 |

TABLE 3-continued

| Structure | NSC Number | Percent Inhibition |
|---|---|---|
| 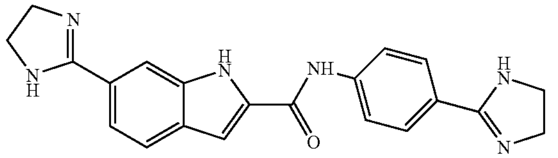 | 294206 | 56 |
| 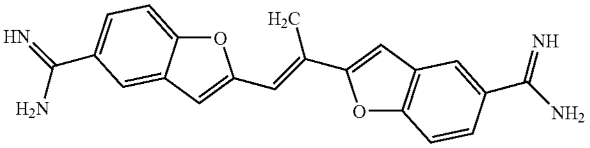 | 266474 | 47 |
| 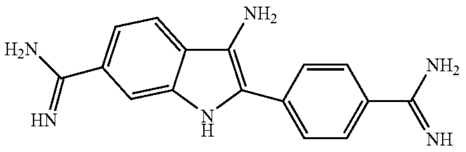 | 300509 | 46 |
| 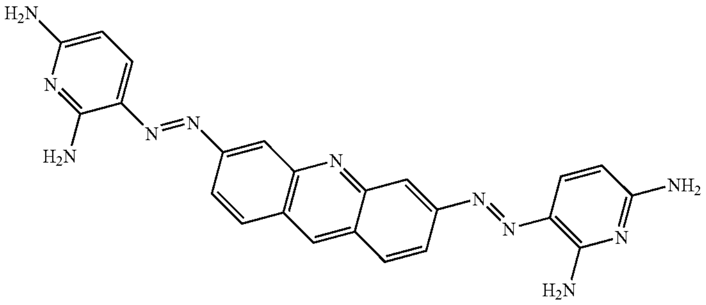 | 354962 | 40 |
| 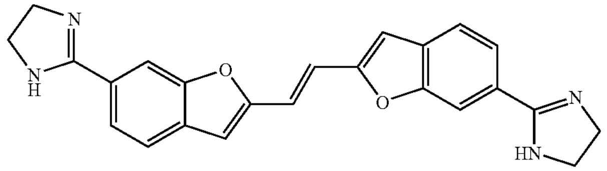 | 294494 | 29 |

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of inhibiting anthrax lethal factor protease activity which comprises contacting at least one compound selected from the group consisting of

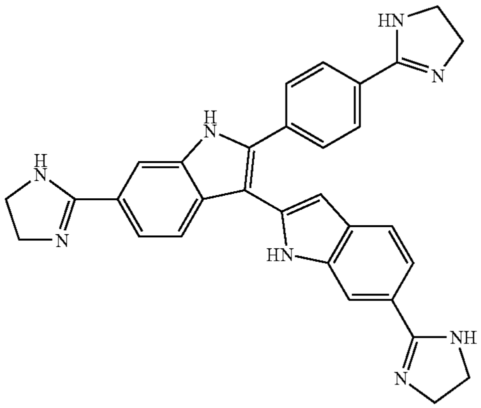

denoted as NSC 341911,

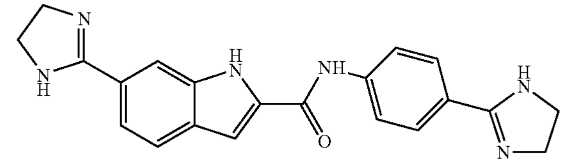
denoted as NSC 294206,
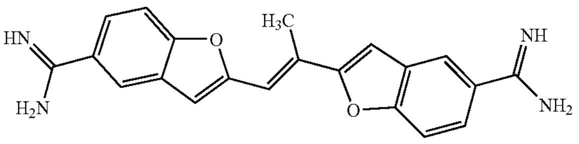
denoted as NSC 300509,
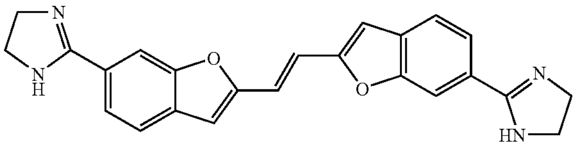
denoted as NSC 294494,
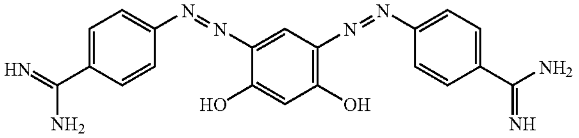
denoted as NSC 359465,
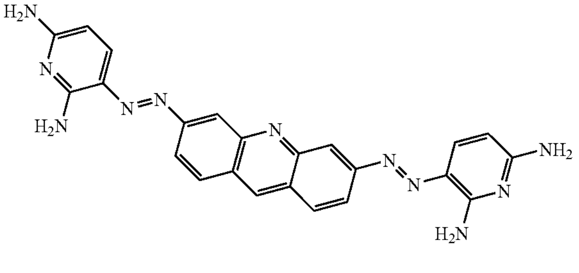
denoted as NSC 354962,
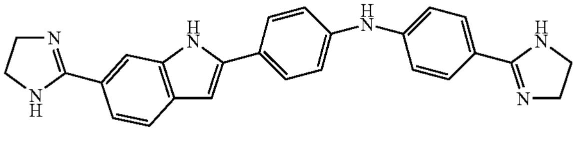
denoted as NSC 377362,
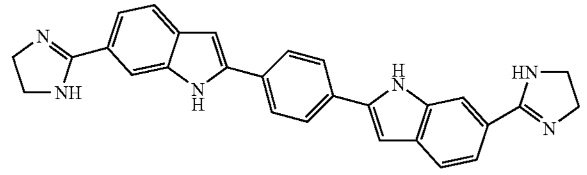
denoted as NSC 317881,
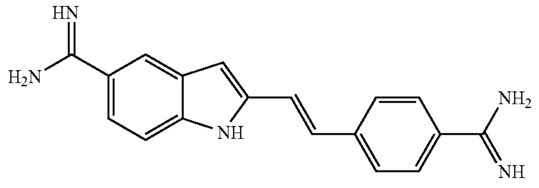
denoted as NSC 317884,
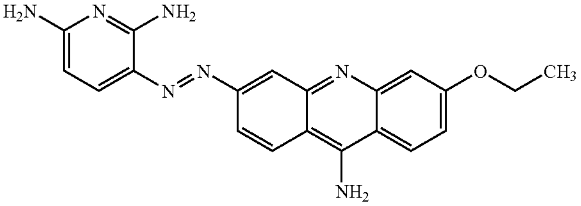
denoted as NSC 354961,
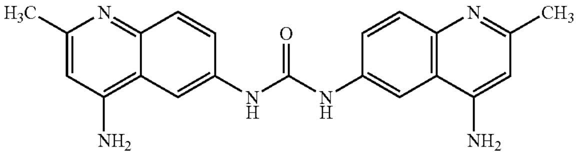
denoted as NSC 12155,
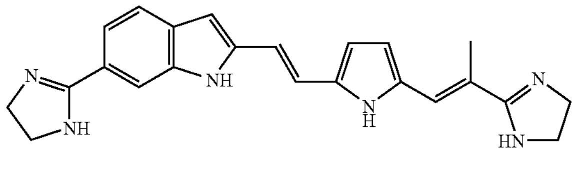
denoted as NSC 317880,
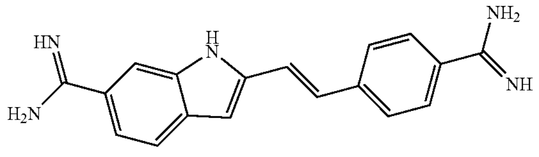
denoted as NSC 317886,

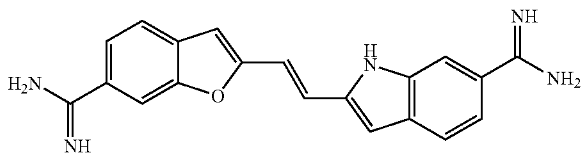
denoted as NSC 294200,
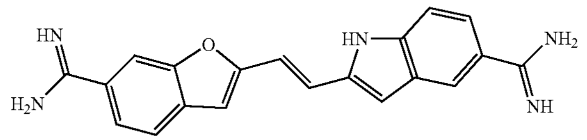
denoted as NSC 294203,
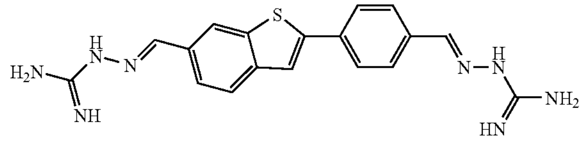
denoted as NSC 341909,
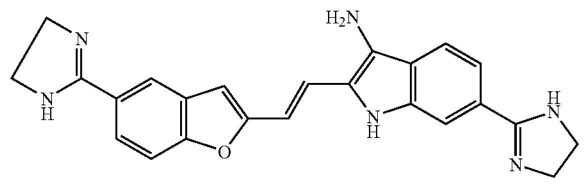
denoted as NSC 357756,
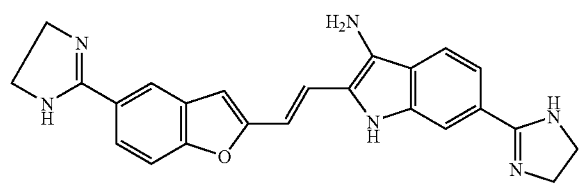
denoted as NSC 369718,
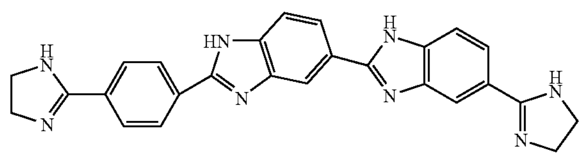
denoted as NSC 369721,
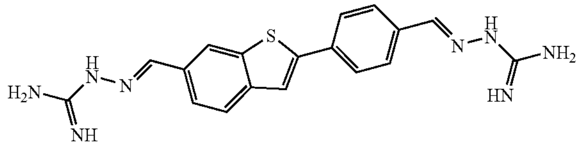
denoted as NSC 294201,
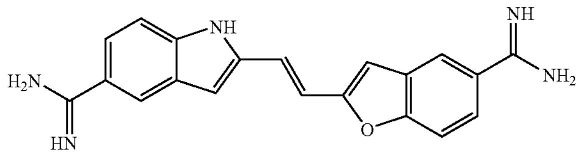
denoted as NSC 290107,
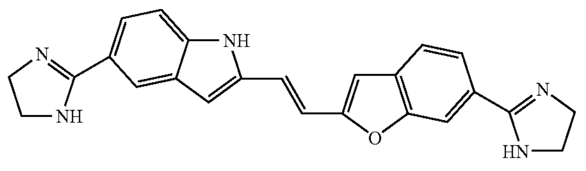
denoted as NSC 294204,
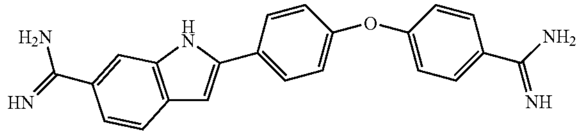
denoted as NSC 240898, and
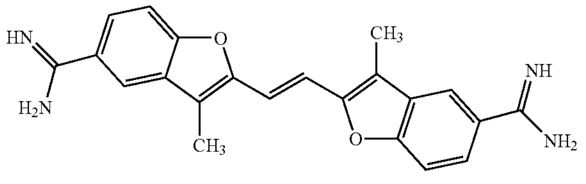
denoted as NSC 266474 with anthrax lethal factor protease.
2. The method of claim 1, wherein the compound is
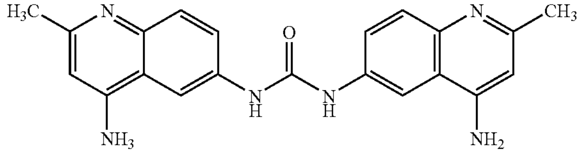
denoted as NSC 12155.
3. The method of claim 2, wherein the compound is in the form of a composition.

4. The method of claim 1, wherein the compound is in the form of a composition.

5. The method of claim 4, wherein the composition further comprises a pharmaceutically acceptable carrier.

6. The method of claim 4, wherein the composition further comprises a supplementary active compound.

* * * * *